(12) United States Patent
Andrews et al.

(10) Patent No.: US 11,701,268 B2
(45) Date of Patent: Jul. 18, 2023

(54) APPARATUS AND METHOD OF MANUFACTURING AN ELASTIC COMPOSITE STRUCTURE FOR AN ABSORBENT SANITARY PRODUCT

(71) Applicant: Curt G. Joa, Inc., Sheboygan Falls, WI (US)

(72) Inventors: Robert Earl Andrews, Sheboygan, WI (US); David Edward Schuette, Kiel, WI (US); Jeffrey Wayne Fritz, Plymouth, WI (US); Justin Marshall Lafferty, Sheboygan, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 0 days.

(21) Appl. No.: 16/260,259

(22) Filed: Jan. 29, 2019

(65) Prior Publication Data
US 2019/0231606 A1 Aug. 1, 2019

Related U.S. Application Data

(60) Provisional application No. 62/666,508, filed on May 3, 2018, provisional application No. 62/623,381, filed on Jan. 29, 2018.

(51) Int. Cl.
*A61F 13/15* (2006.01)
*B32B 37/00* (2006.01)
(Continued)

(52) U.S. Cl.
CPC .. *A61F 13/15593* (2013.01); *A61F 13/15699* (2013.01); *A61F 13/15723* (2013.01);
(Continued)

(58) Field of Classification Search
CPC .......... A61F 13/15593; A61F 13/15699; A61F 13/15739; B32B 37/00; Y10T 156/1054
See application file for complete search history.

(56) References Cited

U.S. PATENT DOCUMENTS

| | | | |
|---|---|---|---|
| 3,580,783 A | 5/1971 | Glaze | |
| 3,622,434 A | 11/1971 | Newman | |

(Continued)

FOREIGN PATENT DOCUMENTS

| | | |
|---|---|---|
| CN | 101868210 B | 9/2014 |
| EP | 0274752 A3 | 5/1990 |

(Continued)

OTHER PUBLICATIONS

Presentation by Thomas Ehlert, VP of RD&E, Aurizon Ultrasonics, LLC, entitled "Adhesive-free, Ultrasonic Elastic Attachment", date at least as early as Nov. 17, 2014, 57 pages.

(Continued)

*Primary Examiner* — George R Koch
*Assistant Examiner* — Christopher C Caillouet
(74) *Attorney, Agent, or Firm* — Klintworth & Rozenblat IP LLP

(57) ABSTRACT

An apparatus for manufacturing an elastic composite structure for an absorbent sanitary product includes an anvil with weld pattern comprising at least one anchoring region and at least one deactivating region. The anchoring region includes anchoring welds that form anchoring bonds that fuse facing web layers and anchor elastic thread(s) in position relative to the facing web layers. The deactivating region includes a break bar constructed to sever the thread(s). A method of manufacturing the elastic composite structure includes positioning a tensioned elastic thread between web layers, fusing the web layers to form an anchored zone that includes anchoring bonds that fuse the web layers and anchor the (Continued)

tensioned elastic thread therebetween, and cutting the thread to form a deactivated zone between adjacent portions of the anchored zone that is free of tensioned threads. The method further includes fusing the web layers within the deactivated zone.

9 Claims, 22 Drawing Sheets

(51) Int. Cl.
  *A61F 13/49* (2006.01)
  *B29C 65/08* (2006.01)
  *B05C 3/12* (2006.01)
  *B26D 1/62* (2006.01)

(52) U.S. Cl.
  CPC .... *A61F 13/15739* (2013.01); *A61F 13/4902* (2013.01); *B29C 65/08* (2013.01); *B32B 37/00* (2013.01); *B05C 3/12* (2013.01); *B26D 1/626* (2013.01); *Y10T 156/1054* (2015.01)

(56) References Cited

U.S. PATENT DOCUMENTS

| | | | |
|---|---|---|---|
| 3,658,064 A | 4/1972 | Pociluyko | |
| 3,668,054 A | 6/1972 | Stumpf | |
| 3,844,869 A * | 10/1974 | Rust, Jr. | B29C 66/8221 |
| | | | 156/358 |
| 3,884,227 A | 5/1975 | Lutz et al. | |
| 3,982,988 A | 9/1976 | Heimberger | |
| 3,993,532 A | 11/1976 | McDonald et al. | |
| 4,088,731 A | 5/1978 | Groome | |
| 4,305,988 A | 12/1981 | Kocher et al. | |
| 4,305,998 A | 12/1981 | Manty et al. | |
| 4,333,978 A | 6/1982 | Kocher | |
| 4,336,203 A | 6/1982 | Zucker et al. | |
| 4,485,819 A | 12/1984 | Igl | |
| 4,662,005 A | 5/1987 | Grier-Idris | |
| 4,770,656 A | 9/1988 | Proxmire et al. | |
| 4,808,176 A | 2/1989 | Kielpikowski | |
| 4,833,734 A | 5/1989 | Der Estephanian | |
| 4,834,738 A | 5/1989 | Kielpikowski et al. | |
| 4,842,596 A | 6/1989 | Kielpikowski et al. | |
| 4,863,542 A | 9/1989 | Oshefsky et al. | |
| 4,919,738 A | 4/1990 | Ball et al. | |
| 5,094,717 A | 3/1992 | Manning et al. | |
| 5,163,932 A | 11/1992 | Nomura et al. | |
| 5,353,798 A | 10/1994 | Sieben | |
| 5,468,320 A | 11/1995 | Zafiroglu | |
| 5,530,979 A | 7/1996 | Whitley | |
| 5,561,863 A | 10/1996 | Carlson, II | |
| 5,618,378 A * | 4/1997 | Cahill | B41F 19/062 |
| | | | 156/358 |
| 5,624,420 A | 4/1997 | Bridges et al. | |
| 5,643,396 A | 7/1997 | Rajala et al. | |
| 5,660,657 A | 8/1997 | Rajala et al. | |
| 5,694,925 A | 12/1997 | Reese et al. | |
| 5,699,791 A | 12/1997 | Sukiennik et al. | |
| 5,707,470 A | 1/1998 | Rajala et al. | |
| 5,711,847 A | 1/1998 | Rajala et al. | |
| 5,745,922 A | 5/1998 | Rajala et al. | |
| 5,769,993 A | 6/1998 | Baldauf | |
| 5,789,065 A | 8/1998 | Haffner et al. | |
| 5,797,895 A | 8/1998 | Widlund et al. | |
| 5,803,075 A | 9/1998 | Yavitz | |
| 5,813,398 A | 9/1998 | Baird et al. | |
| 5,817,584 A | 10/1998 | Singer et al. | |
| 5,883,026 A | 3/1999 | Reader et al. | |
| 5,934,275 A | 8/1999 | Gazzara | |
| 5,954,055 A | 9/1999 | Miyake | |
| D424,688 S | 5/2000 | Bryant et al. | |
| 6,055,982 A | 5/2000 | Brunson et al. | |
| 6,057,024 A | 5/2000 | Mleziva et al. | |
| 6,062,220 A | 5/2000 | Whitaker et al. | |
| 6,123,077 A | 9/2000 | Bostock et al. | |
| 6,125,849 A | 10/2000 | Williams et al. | |
| 6,165,298 A | 12/2000 | Samida et al. | |
| 6,173,712 B1 | 1/2001 | Brunson | |
| 6,197,404 B1 | 3/2001 | Varona | |
| 6,213,125 B1 | 4/2001 | Reese et al. | |
| 6,217,889 B1 | 4/2001 | Lorenzi et al. | |
| 6,235,137 B1 | 5/2001 | Van Eperen et al. | |
| 6,257,235 B1 | 7/2001 | Bowen | |
| 6,279,570 B1 | 8/2001 | Mittelstadt et al. | |
| 6,291,039 B1 | 9/2001 | Combe et al. | |
| 6,295,714 B1 | 10/2001 | Roychowdhury et al. | |
| 6,332,465 B1 | 12/2001 | Xue et al. | |
| 6,340,782 B1 | 1/2002 | Kling et al. | |
| 6,354,296 B1 | 3/2002 | Baumann et al. | |
| 6,394,090 B1 | 5/2002 | Chen et al. | |
| 6,427,693 B1 | 8/2002 | Blackstock et al. | |
| 6,460,539 B1 | 10/2002 | Japuntich et al. | |
| 6,482,278 B1 | 11/2002 | McCabe et al. | |
| 6,484,722 B2 | 11/2002 | Bostock et al. | |
| 6,506,474 B2 | 1/2003 | Tsuji | |
| 6,534,694 B2 | 3/2003 | Kling et al. | |
| 6,536,434 B1 | 3/2003 | Bostock et al. | |
| 6,541,679 B2 | 4/2003 | Betrabet et al. | |
| 6,568,392 B1 | 5/2003 | Bostock et al. | |
| 6,584,976 B2 | 7/2003 | Japuntich et al. | |
| 6,604,524 B1 | 8/2003 | Curran et al. | |
| 6,613,955 B1 | 9/2003 | Lindsay et al. | |
| 6,623,837 B2 | 9/2003 | Morman et al. | |
| 6,644,314 B1 | 11/2003 | Elsberg | |
| 6,652,693 B2 | 11/2003 | Burriss et al. | |
| 6,673,980 B1 | 1/2004 | Varona et al. | |
| 6,712,922 B2 | 3/2004 | Sorenson et al. | |
| 6,715,489 B2 | 4/2004 | Bostock et al. | |
| 6,722,366 B2 | 4/2004 | Bostock et al. | |
| 6,730,188 B2 | 5/2004 | Sanders | |
| 6,761,710 B2 | 7/2004 | D'Acchioli et al. | |
| 6,780,263 B2 | 8/2004 | Delisle | |
| 6,843,872 B2 | 1/2005 | Morman | |
| 6,886,563 B2 | 5/2005 | Bostock et al. | |
| 6,889,622 B2 | 5/2005 | Marcangelo | |
| 6,914,018 B1 | 7/2005 | Uitenbroek et al. | |
| 6,928,657 B2 | 8/2005 | Bell et al. | |
| 6,953,452 B2 | 10/2005 | Popp et al. | |
| 7,008,496 B2 | 3/2006 | Morman | |
| 7,021,227 B2 | 4/2006 | Marcangelo | |
| 7,025,841 B2 | 4/2006 | Owen | |
| 7,044,131 B2 | 5/2006 | Griesbach et al. | |
| 7,069,930 B2 | 7/2006 | Bostock et al. | |
| 7,118,558 B2 * | 10/2006 | Wu | B05C 3/12 |
| | | | 604/385.29 |
| 7,198,688 B2 | 4/2007 | Mortell et al. | |
| 7,211,531 B2 | 5/2007 | Schneider et al. | |
| 7,217,261 B2 | 5/2007 | Otsubo et al. | |
| 7,290,545 B2 | 11/2007 | Kleman et al. | |
| 7,316,840 B2 | 1/2008 | Neculescu et al. | |
| 7,361,241 B2 | 4/2008 | Barth et al. | |
| 7,378,566 B2 | 5/2008 | Soerens et al. | |
| 7,469,427 B2 | 12/2008 | Yang et al. | |
| 7,507,680 B2 | 3/2009 | Middlesworth et al. | |
| 7,582,348 B2 * | 9/2009 | Ando | A61F 13/4902 |
| | | | 428/103 |
| 7,617,787 B2 | 11/2009 | Marcangelo | |
| 7,619,167 B2 | 11/2009 | Lee et al. | |
| 7,638,014 B2 | 12/2009 | Coose et al. | |
| 7,642,398 B2 | 1/2010 | Jarpenberg et al. | |
| 7,691,138 B2 | 4/2010 | Stenzel et al. | |
| 7,708,849 B2 | 5/2010 | McCabe | |
| 7,722,734 B2 | 5/2010 | Otsubo | |
| 7,725,948 B2 | 6/2010 | Steindorf | |
| 7,799,967 B2 | 9/2010 | Ranganathan et al. | |
| 7,833,369 B2 | 11/2010 | Zhou et al. | |
| 7,845,351 B2 | 12/2010 | Mathis et al. | |
| 7,861,756 B2 | 1/2011 | Jenquin et al. | |
| 7,901,392 B2 | 3/2011 | Kline et al. | |
| 7,955,418 B2 | 6/2011 | Claussen et al. | |
| 7,981,231 B2 | 7/2011 | Schneider et al. | |
| 8,007,484 B2 | 8/2011 | McCabe et al. | |

(56) References Cited

U.S. PATENT DOCUMENTS

| | | | |
|---|---|---|---|
| 8,074,660 B2 | 12/2011 | Duffy |
| 8,075,543 B2 | 12/2011 | Okuda |
| 8,091,550 B2 | 1/2012 | Steindorf |
| 8,109,916 B2 | 2/2012 | Wennerback |
| 8,142,411 B2 | 3/2012 | Kline et al. |
| 8,146,594 B2 | 4/2012 | Bostock et al. |
| 8,182,624 B2 | 5/2012 | Handziak |
| 8,207,395 B2 | 6/2012 | Soerens et al. |
| 8,268,444 B2 | 9/2012 | Okaya |
| 8,282,617 B2 | 10/2012 | Kaneda et al. |
| 8,298,205 B2 | 10/2012 | Norrby et al. |
| 8,308,706 B2 | 11/2012 | Fukae |
| 8,323,257 B2 | 12/2012 | Melik et al. |
| 8,328,820 B2 | 12/2012 | Diamant et al. |
| 8,360,067 B2 | 1/2013 | Duffy |
| 8,375,950 B2 | 2/2013 | Bostock et al. |
| 8,435,223 B2 | 5/2013 | Roe et al. |
| 8,440,043 B1 | 5/2013 | Schneider et al. |
| 8,470,946 B1 | 6/2013 | Carlson |
| 8,528,560 B2 | 9/2013 | Duffy |
| 8,562,777 B2 * | 10/2013 | Drake ............... D06P 5/004 |
| | | | 156/230 |
| 8,585,667 B2 | 11/2013 | Roe et al. |
| 8,622,059 B2 | 1/2014 | Kleman |
| 8,640,704 B2 | 2/2014 | Spoo et al. |
| 8,647,319 B2 | 2/2014 | Een et al. |
| 8,652,114 B2 | 2/2014 | Roe et al. |
| 8,652,115 B2 | 2/2014 | Roe et al. |
| 8,669,409 B2 | 3/2014 | Roe |
| 8,741,083 B2 | 6/2014 | Wennerback et al. |
| 8,758,786 B2 | 6/2014 | Hassler |
| 8,771,449 B2 | 7/2014 | Takino et al. |
| 8,784,395 B2 | 7/2014 | Roe et al. |
| 8,784,397 B2 | 7/2014 | Chang et al. |
| 8,808,263 B2 | 8/2014 | Roe et al. |
| 8,881,729 B2 | 11/2014 | Duffy |
| 8,926,579 B2 | 1/2015 | Wang et al. |
| 8,932,273 B2 | 1/2015 | Roe et al. |
| 8,936,586 B2 | 1/2015 | Roe |
| 8,992,497 B2 | 3/2015 | Roe et al. |
| 8,998,870 B2 | 4/2015 | Roe |
| 9,011,402 B2 | 4/2015 | Roe et al. |
| 9,011,404 B2 | 4/2015 | Kobayashi et al. |
| 9,012,013 B2 | 4/2015 | Duffy |
| 9,028,462 B2 | 5/2015 | Poole et al. |
| 9,056,033 B2 | 6/2015 | Fenske |
| 9,060,905 B2 | 6/2015 | Wang et al. |
| 9,078,789 B2 | 7/2015 | Wang et al. |
| 9,078,792 B2 | 7/2015 | Ruiz |
| 9,089,456 B2 | 7/2015 | Roe et al. |
| 9,095,478 B2 | 8/2015 | Roe |
| 9,180,059 B2 | 11/2015 | Roe et al. |
| 9,301,881 B2 | 4/2016 | Ando et al. |
| 9,387,138 B2 | 7/2016 | Roe |
| 9,539,735 B2 | 1/2017 | Ferguson et al. |
| 9,603,395 B2 | 3/2017 | Duffy |
| 9,603,396 B2 | 3/2017 | Duffy |
| 9,615,612 B2 | 4/2017 | Duffy |
| 9,770,057 B2 | 9/2017 | Duffy |
| 9,770,058 B2 | 9/2017 | Angadjivand et al. |
| 9,770,611 B2 | 9/2017 | Facer et al. |
| 9,809,414 B2 | 11/2017 | Fritz et al. |
| 9,868,002 B2 | 1/2018 | Duffy |
| 9,913,764 B2 * | 3/2018 | Thomas ............... A61F 13/4902 |
| 10,040,621 B2 | 8/2018 | Duffy et al. |
| 10,130,833 B2 | 11/2018 | Angadjivand et al. |
| 10,137,321 B2 | 11/2018 | Martin |
| 10,143,246 B2 | 12/2018 | Houde et al. |
| D837,970 S | 1/2019 | Henderson et al. |
| 10,182,603 B2 | 1/2019 | Duffy |
| 10,213,348 B2 | 2/2019 | Gualtieri et al. |
| 10,227,202 B2 | 3/2019 | Pamperin et al. |
| 10,259,165 B2 | 4/2019 | Ehlert et al. |
| D848,678 S | 5/2019 | Andrews |
| 10,314,346 B2 | 6/2019 | Potnis et al. |
| 10,457,436 B2 | 10/2019 | Spencer et al. |
| 10,492,547 B2 | 12/2019 | Weber et al. |
| 10,494,221 B2 | 12/2019 | Harris et al. |
| 10,537,479 B2 | 1/2020 | Schuette et al. |
| 10,596,045 B2 | 3/2020 | Koshijima et al. |
| 10,596,047 B2 | 3/2020 | Coenen et al. |
| 10,751,228 B2 | 8/2020 | Kurohara et al. |
| 10,758,428 B2 | 9/2020 | Nakamura et al. |
| 10,786,398 B2 | 9/2020 | Koshijima et al. |
| 10,792,194 B2 | 10/2020 | Hohm et al. |
| 10,889,066 B2 | 1/2021 | Begrow et al. |
| 10,893,986 B2 | 1/2021 | Manabe et al. |
| 10,973,703 B2 | 4/2021 | Coenen et al. |
| 11,020,281 B2 | 6/2021 | Ishikawa |
| 11,020,286 B2 | 6/2021 | Kaufman et al. |
| 11,129,753 B2 | 9/2021 | Schneider et al. |
| 11,141,321 B2 | 10/2021 | Schneider et al. |
| 11,147,717 B2 | 10/2021 | Schneider et al. |
| 11,173,072 B2 | 11/2021 | Fritz |
| 11,191,676 B2 | 12/2021 | Koshijima et al. |
| 11,219,555 B2 | 1/2022 | Schneider et al. |
| 11,254,062 B2 | 2/2022 | Ehlert et al. |
| 11,254,066 B2 | 2/2022 | Row et al. |
| 11,399,989 B2 | 8/2022 | Polidori et al. |
| 11,433,620 B2 | 9/2022 | Ehlert et al. |
| 2001/0025683 A1 * | 10/2001 | Burriss ............... B05C 5/0241 |
| | | | 156/163 |
| 2001/0034508 A1 | 10/2001 | Betrabet et al. |
| 2001/0044250 A1 | 11/2001 | Tsuji |
| 2002/0092604 A1 | 7/2002 | McCabe et al. |
| 2002/0116027 A1 | 8/2002 | Egan et al. |
| 2002/0119288 A1 | 8/2002 | Morman et al. |
| 2002/0157778 A1 | 10/2002 | Sorenson et al. |
| 2003/0051803 A1 | 3/2003 | Sanders |
| 2003/0120250 A1 | 6/2003 | Betrabet et al. |
| 2003/0124306 A1 | 7/2003 | Morman |
| 2003/0125706 A1 | 7/2003 | Popp et al. |
| 2003/0125707 A1 | 7/2003 | Popp et al. |
| 2003/0135185 A1 | 7/2003 | Crowther |
| 2003/0144643 A1 | 7/2003 | Jarpenberg et al. |
| 2004/0005832 A1 | 1/2004 | Neculescu et al. |
| 2004/0059280 A1 | 3/2004 | Makower et al. |
| 2004/0112509 A1 | 6/2004 | Morman |
| 2004/0116885 A1 | 6/2004 | Soerens et al. |
| 2004/0127614 A1 | 7/2004 | Jiang et al. |
| 2004/0138635 A1 | 7/2004 | Sorenson et al. |
| 2004/0158217 A1 | 8/2004 | Wu et al. |
| 2004/0192140 A1 | 9/2004 | Schneider et al. |
| 2004/0219854 A1 | 11/2004 | Groitzsch et al. |
| 2004/0226645 A1 | 11/2004 | Owen |
| 2004/0243085 A1 | 12/2004 | Veith et al. |
| 2004/0261230 A1 | 12/2004 | Neeb et al. |
| 2005/0095942 A1 | 5/2005 | Mueller et al. |
| 2005/0101216 A1 | 5/2005 | Middlesworth et al. |
| 2005/0131374 A1 | 6/2005 | Otsubo et al. |
| 2005/0142331 A1 | 6/2005 | Anderson et al. |
| 2005/0148261 A1 | 7/2005 | Close et al. |
| 2005/0176029 A1 | 8/2005 | Heller et al. |
| 2005/0183646 A1 | 8/2005 | Marcangelo |
| 2005/0216058 A1 | 9/2005 | Egan et al. |
| 2005/0228350 A1 | 10/2005 | Ranganathan et al. |
| 2006/0009104 A1 | 1/2006 | Schneider et al. |
| 2006/0069373 A1 | 3/2006 | Schlinz et al. |
| 2006/0099871 A1 | 5/2006 | Poruthoor et al. |
| 2006/0130964 A1 | 6/2006 | McCabe |
| 2006/0135923 A1 | 6/2006 | Boggs et al. |
| 2006/0135932 A1 | 6/2006 | Abuto et al. |
| 2006/0138693 A1 | 6/2006 | Tuman et al. |
| 2006/0149208 A1 | 7/2006 | Carr |
| 2006/0180068 A1 | 8/2006 | Marcangelo |
| 2006/0224137 A1 | 10/2006 | McCabe et al. |
| 2006/0228969 A1 | 10/2006 | Erdman et al. |
| 2006/0238757 A1 | 10/2006 | Silcott |
| 2006/0270302 A1 | 11/2006 | Ando et al. |
| 2007/0000021 A1 | 1/2007 | Yang et al. |
| 2007/0068529 A1 | 3/2007 | Kalatoor et al. |
| 2007/0131335 A1 | 6/2007 | Zhou et al. |
| 2007/0175477 A1 | 8/2007 | Baggett |
| 2007/0218245 A1 | 9/2007 | Schneider et al. |

(56) References Cited

U.S. PATENT DOCUMENTS

| | | |
|---|---|---|
| 2007/0286987 A1 | 12/2007 | Anderson et al. |
| 2008/0103460 A1 | 5/2008 | Close et al. |
| 2008/0110554 A1 | 5/2008 | Otsubo |
| 2008/0262455 A1 | 10/2008 | Soerens et al. |
| 2009/0134049 A1 | 5/2009 | Melik et al. |
| 2009/0163940 A1 | 6/2009 | Sliwa |
| 2009/0208703 A1 | 8/2009 | Wennerback et al. |
| 2009/0242098 A1 | 10/2009 | Handziak |
| 2009/0306616 A1 | 12/2009 | Wennerback |
| 2009/0326503 A1 | 12/2009 | Lakso et al. |
| 2009/0326504 A1 | 12/2009 | Kaneda |
| 2010/0015190 A1 | 1/2010 | Hassler |
| 2010/0076390 A1 | 3/2010 | Norrby et al. |
| 2010/0076394 A1 | 3/2010 | Hayase et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerback |
| 2011/0055998 A1 | 3/2011 | Tai et al. |
| 2011/0061786 A1 | 3/2011 | Mason |
| 2011/0067797 A1 | 3/2011 | Schneider et al. |
| 2011/0118689 A1 | 5/2011 | Een et al. |
| 2011/0152811 A1 | 6/2011 | Bing-Wo et al. |
| 2011/0184372 A1 | 7/2011 | Ostlin et al. |
| 2011/0192888 A1 | 8/2011 | Tai et al. |
| 2011/0251576 A1 | 10/2011 | Ando et al. |
| 2011/0257616 A1 | 10/2011 | Lakso et al. |
| 2012/0088103 A1 | 4/2012 | Sugiura et al. |
| 2012/0095429 A1 | 4/2012 | Kobayashi et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0175064 A1* | 7/2012 | Yamamoto .......... B29C 66/1122 156/379.6 |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2013/0255865 A1 | 10/2013 | Brown et al. |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2015/0164705 A1* | 6/2015 | Thomas ............ A61F 13/15593 428/172 |
| 2016/0058624 A1 | 3/2016 | Hohm et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0113366 A1 | 4/2017 | Ferguson et al. |
| 2017/0281417 A1 | 10/2017 | Ishikawa |
| 2018/0027899 A1 | 2/2018 | Facer et al. |
| 2018/0042788 A1 | 2/2018 | Kurohara et al. |
| 2018/0093444 A1 | 4/2018 | Begrow et al. |
| 2018/0140473 A1 | 5/2018 | Koshijima et al. |
| 2018/0147095 A1 | 5/2018 | Koshijima et al. |
| 2018/0168880 A1 | 6/2018 | Schneider et al. |
| 2018/0169964 A1* | 6/2018 | Schneider .......... A61F 13/4902 |
| 2018/0170027 A1 | 6/2018 | Schneider et al. |
| 2018/0280209 A1 | 10/2018 | Manabe et al. |
| 2019/0000162 A1 | 1/2019 | Houde |
| 2019/0021916 A1* | 1/2019 | Ishikawa .......... B29C 66/83411 |
| 2019/0070041 A1 | 3/2019 | Schneider et al. |
| 2019/0209396 A1 | 7/2019 | Nakamura et al. |
| 2019/0224053 A1 | 7/2019 | Nakamura et al. |
| 2019/0231606 A1 | 8/2019 | Andrews et al. |
| 2019/0274895 A1 | 9/2019 | Chen et al. |
| 2019/0358093 A1 | 11/2019 | Kaufman et al. |
| 2019/0374398 A1* | 12/2019 | Coenen ............ A61F 13/49015 |
| 2019/0374404 A1 | 12/2019 | Ninomiya et al. |
| 2020/0039152 A1 | 2/2020 | Ehlert et al. |
| 2020/0179180 A1 | 6/2020 | Koshijima et al. |
| 2020/0197230 A1 | 6/2020 | Ohtsubo |
| 2020/0206040 A1 | 7/2020 | Andrews et al. |
| 2020/0206043 A1 | 7/2020 | Coenen et al. |
| 2020/0214901 A1 | 7/2020 | Andrews et al. |
| 2020/0268567 A1 | 8/2020 | Coenen et al. |
| 2020/0297551 A1 | 9/2020 | Andrews et al. |
| 2020/0298545 A1 | 9/2020 | Andrews et al. |
| 2020/0299883 A1 | 9/2020 | Begrow et al. |
| 2020/0360191 A1 | 11/2020 | Nakamura et al. |
| 2020/0361158 A1 | 11/2020 | Sugiura et al. |
| 2021/0000657 A1 | 1/2021 | Hohm et al. |
| 2021/0059866 A1 | 3/2021 | Fritz et al. |
| 2021/0100695 A1 | 4/2021 | Ishibashi et al. |
| 2021/0205152 A1 | 7/2021 | Polidori et al. |
| 2021/0252796 A1 | 8/2021 | Ehlert et al. |
| 2021/0267818 A1 | 9/2021 | Kaufman et al. |
| 2022/0000676 A1 | 1/2022 | Schneider et al. |
| 2022/0071809 A1 | 3/2022 | Fritz |
| 2022/0151840 A1 | 5/2022 | Mueller et al. |
| 2022/0211553 A1 | 7/2022 | Manabe |
| 2022/0218534 A1 | 7/2022 | Minami et al. |
| 2022/0250331 A1 | 8/2022 | Weiler et al. |

FOREIGN PATENT DOCUMENTS

| | | |
|---|---|---|
| EP | 0168225 B1 | 3/1991 |
| EP | 0330716 A3 | 7/1991 |
| EP | 0307871 B1 | 12/1992 |
| EP | 0386324 B1 | 6/1993 |
| EP | 685586 A2 | 12/1995 |
| EP | 0677284 B1 | 6/1999 |
| EP | 0886480 B1 | 12/2001 |
| EP | 1166721 A3 | 12/2003 |
| EP | 1035808 B1 | 3/2004 |
| EP | 1024721 B1 | 9/2004 |
| EP | 1351815 B9 | 6/2005 |
| EP | 1388410 B1 | 10/2005 |
| EP | 1448824 B1 | 10/2005 |
| EP | 1236827 B1 | 1/2006 |
| EP | 1029521 B1 | 4/2006 |
| EP | 1138471 B1 | 6/2006 |
| EP | 1159942 B1 | 7/2006 |
| EP | 1641417 B1 | 6/2007 |
| EP | 1547558 B1 | 10/2008 |
| EP | 1555000 A3 | 11/2008 |
| EP | 1290289 B1 | 12/2008 |
| EP | 1330355 B1 | 3/2009 |
| EP | 1263989 B1 | 5/2009 |
| EP | 1458553 B1 | 9/2009 |
| EP | 1330222 B8 | 10/2009 |
| EP | 1610950 B1 | 10/2009 |
| EP | 1715994 B1 | 3/2010 |
| EP | 1520569 B1 | 7/2010 |
| EP | 1586252 B1 | 8/2010 |
| EP | 1959907 B1 | 9/2010 |
| EP | 1525345 B1 | 4/2011 |
| EP | 1882177 B1 | 6/2011 |
| EP | 1707168 B1 | 8/2011 |
| EP | 1716831 B1 | 9/2011 |
| EP | 2083100 B1 | 9/2011 |
| EP | 2207926 B1 | 9/2011 |
| EP | 2219534 B1 | 9/2011 |
| EP | 2027841 B1 | 7/2012 |
| EP | 1595017 B1 | 8/2012 |
| EP | 1891256 B1 | 8/2012 |
| EP | 2020972 B1 | 11/2012 |
| EP | 2020974 B1 | 12/2012 |
| EP | 1685816 B1 | 1/2013 |
| EP | 2024178 B1 | 1/2013 |
| EP | 2088980 B1 | 1/2013 |
| EP | 2103427 A3 | 3/2013 |
| EP | 1272347 B1 | 4/2013 |

(56) References Cited

FOREIGN PATENT DOCUMENTS

| | | | |
|---|---|---|---|
| EP | 1458565 | B1 | 3/2014 |
| EP | 1575470 | B1 | 6/2014 |
| EP | 2088981 | B1 | 6/2014 |
| EP | 2431013 | B1 | 9/2014 |
| EP | 2441866 | B1 | 2/2015 |
| EP | 2727521 | A4 | 3/2015 |
| EP | 1806117 | B1 | 6/2016 |
| EP | 3028687 | A1 | 6/2016 |
| EP | 3092997 | A1 | 11/2016 |
| EP | 1666178 | B1 | 5/2017 |
| EP | 2214614 | B1 | 8/2017 |
| EP | 2450015 | B1 | 11/2017 |
| EP | 2105115 | B1 | 3/2018 |
| EP | 2116367 | B1 | 4/2018 |
| EP | 2142261 | B1 | 5/2018 |
| EP | 2454957 | B1 | 11/2018 |
| EP | 3277480 | A4 | 3/2019 |
| EP | 3117810 | B1 | 7/2019 |
| EP | 3199132 | B1 | 9/2019 |
| EP | 3056176 | B1 | 10/2019 |
| EP | 3296100 | B1 | 1/2020 |
| EP | 3527181 | A4 | 6/2020 |
| EP | 3675784 | A1 | 7/2020 |
| EP | 3677231 | A1 | 7/2020 |
| EP | 3558192 | B1 | 1/2021 |
| EP | 3589251 | A4 | 1/2021 |
| EP | 3589252 | A4 | 1/2021 |
| EP | 3646830 | A4 | 3/2021 |
| EP | 3558664 | B1 | 4/2021 |
| EP | 3519162 | B1 | 7/2021 |
| EP | 3572052 | B1 | 7/2021 |
| EP | 3558193 | B1 | 8/2021 |
| EP | 3727254 | A4 | 8/2021 |
| EP | 3865103 | A1 | 8/2021 |
| EP | 3558191 | B1 | 9/2021 |
| EP | 3275413 | B1 | 10/2021 |
| EP | 3342385 | B1 | 10/2021 |
| EP | 3527182 | B1 | 10/2021 |
| EP | 3675785 | B1 | 11/2021 |
| EP | 3904057 | A1 | 11/2021 |
| EP | 3747636 | A4 | 12/2021 |
| EP | 3941738 | A1 | 1/2022 |
| EP | 3299167 | B1 | 3/2022 |
| EP | 3981371 | A1 | 4/2022 |
| EP | 3960439 | A4 | 6/2022 |
| EP | 3960140 | A4 | 7/2022 |
| EP | 4025412 | A1 | 7/2022 |
| FR | 2532337 | A1 | 3/1984 |
| JP | 2005095574 | A | 4/2005 |
| JP | 2008154998 | A | 7/2008 |
| JP | 2009056156 | A | 3/2009 |
| JP | 2009106667 | A | 5/2009 |
| JP | 5085239 | B2 | 11/2012 |
| JP | 05106990 | B2 | 12/2012 |
| JP | 05124188 | B2 | 1/2013 |
| JP | 2014198179 | A | 10/2014 |
| JP | 2017064130 | A | 4/2017 |
| JP | 06192003 | B2 | 9/2017 |
| KR | 1982464 | B1 | 5/2019 |
| KR | 2013608 | B1 | 8/2019 |
| KR | 2022211 | B1 | 9/2019 |
| RU | 2304047 | C2 | 8/2007 |
| RU | 2010125133 | C2 | 5/2012 |
| WO | WO9321788 | A1 | 11/1993 |
| WO | WO0192013 | A1 | 12/2001 |
| WO | 2009067055 | A1 | 5/2009 |
| WO | 2011087502 | A1 | 7/2011 |
| WO | WO2014109924 | A1 | 7/2014 |
| WO | 2016033226 | A1 | 3/2016 |
| WO | 2016109514 | A1 | 7/2016 |
| WO | WO2016160752 | A1 | 10/2016 |
| WO | 2016208513 | A1 | 12/2016 |
| WO | WO2018097771 | A1 | 5/2018 |
| WO | WO2018118573 | A1 | 6/2018 |
| WO | WO2019070248 | A1 | 4/2019 |
| WO | WO2019125415 | A1 | 6/2019 |

OTHER PUBLICATIONS

PCT International Search Report and Written Opinion(1800.182_PCT), dated Jun. 4, 2021.

Japanese Office Action for Application No. JP2020-541440 dated Feb. 7, 2023.

* cited by examiner

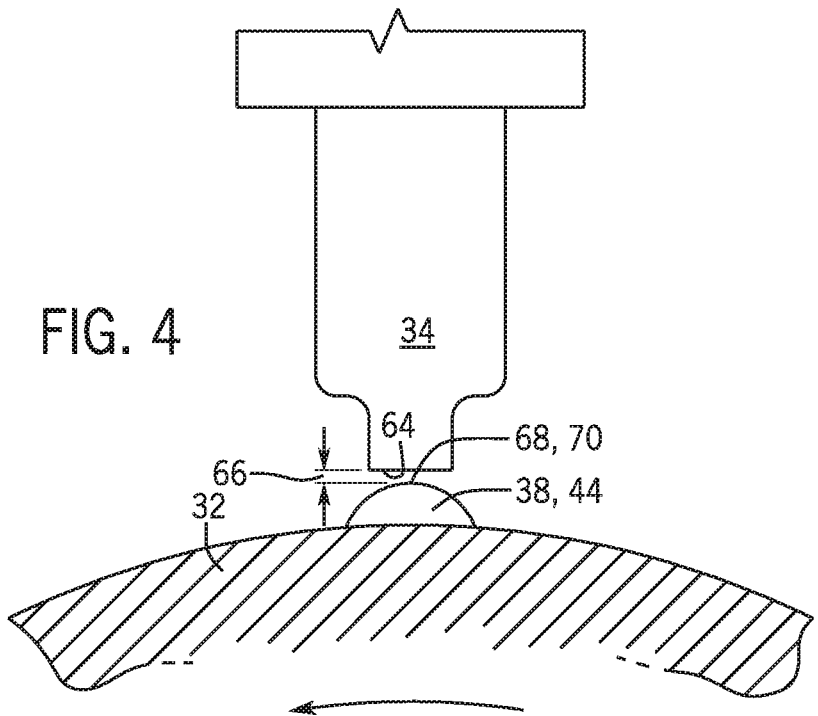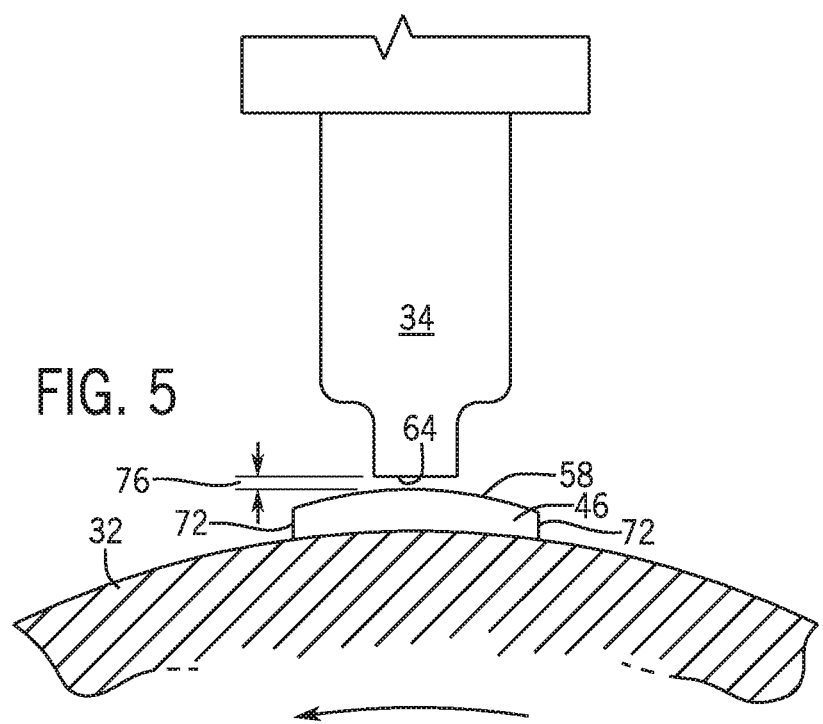

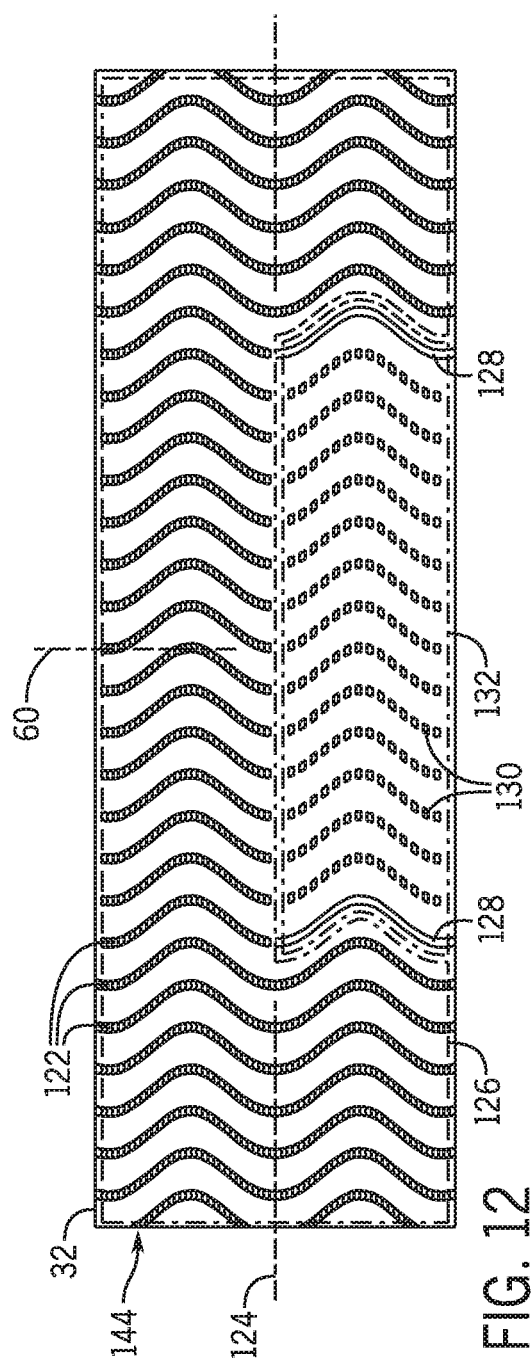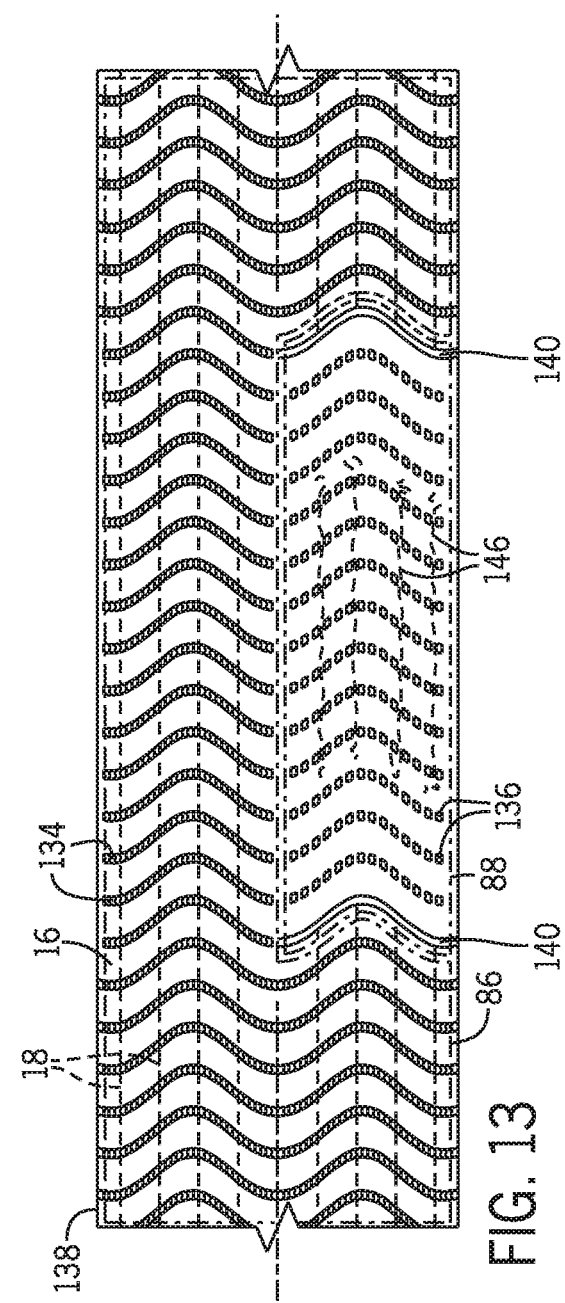

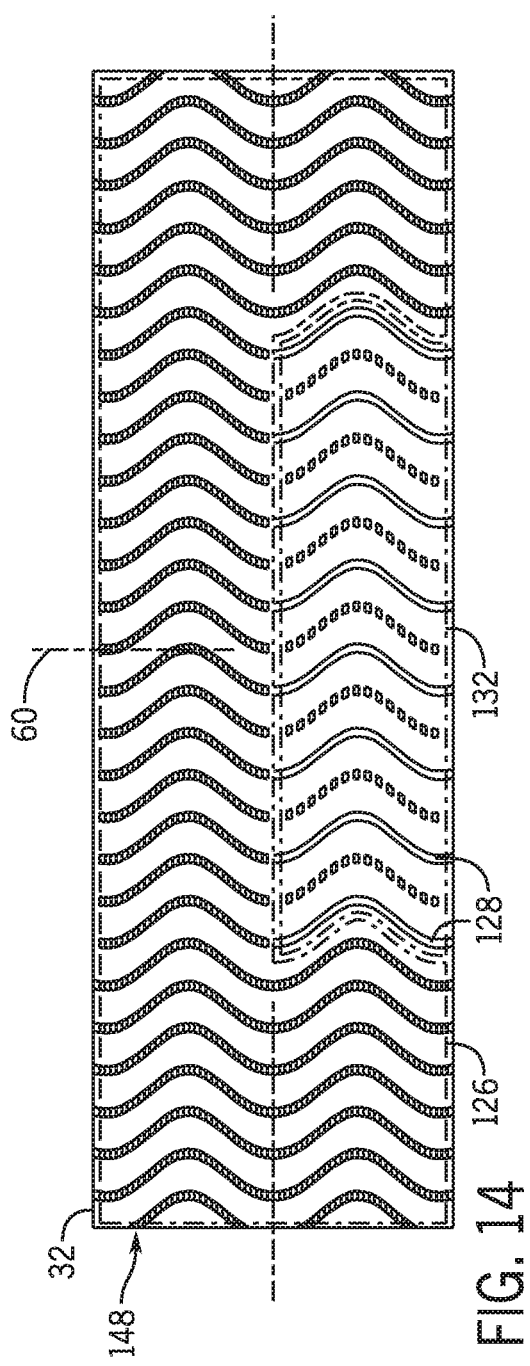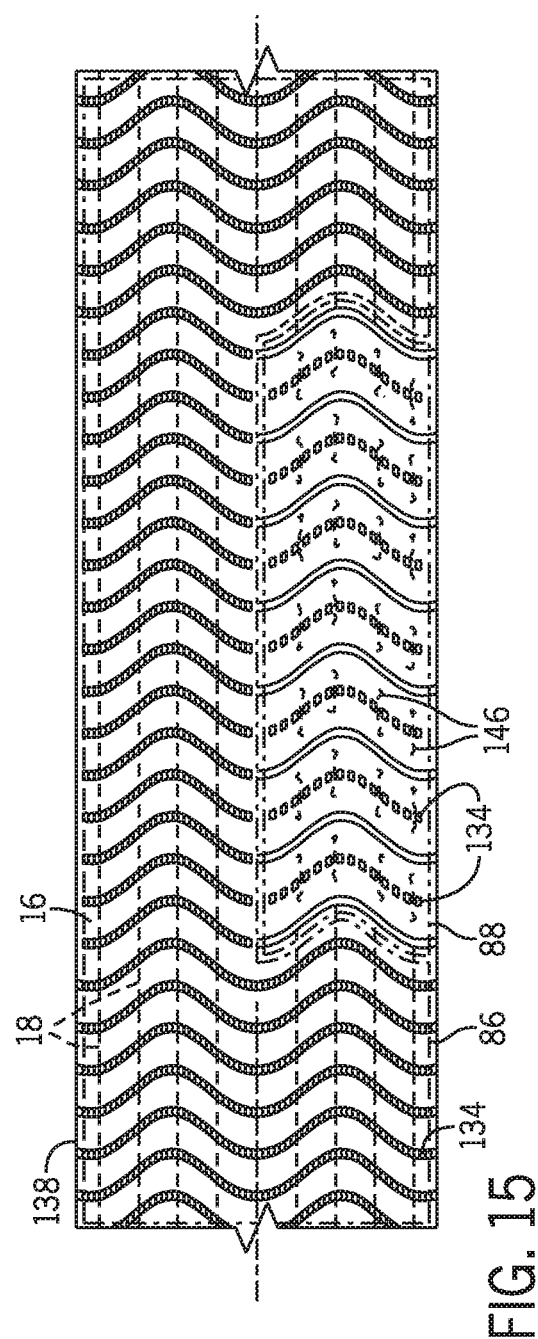

APPARATUS AND METHOD OF MANUFACTURING AN ELASTIC COMPOSITE STRUCTURE FOR AN ABSORBENT SANITARY PRODUCT

CROSS-REFERENCE TO RELATED APPLICATION

The present invention claims the benefit of U.S. Provisional Patent Application Ser. No. 62/623,381, filed Jan. 29, 2018, and to U.S. Provisional Patent Application Ser. No. 62/666,508, filed May 3, 2018, the disclosures of which are incorporated herein by reference in their entireties.

BACKGROUND OF THE INVENTION

Embodiments of the invention relate generally to absorbent sanitary products and, more particularly, to an improved apparatus and method for manufacturing an elastic composite structure for use in an absorbent sanitary product that includes elasticized regions and regions of relative inelasticity while minimizing or eliminating the use of consumable adhesives such as glue.

Absorbent sanitary products, such as disposable diapers, are typically equipped with elastic composite structures that include one or more elastic threads. These elastic composite structures are positioned at various locations throughout the product, including in the waistbands, leg cuff regions, and throughout all or portions of the front or back panels of the product. During the typical manufacturing process of an elastic composite structure, the elastic threads are held in a tensioned state and an adhesive is used to secure the elastic threads between the two facing layers of non-woven materials or webs. The tension in the elastic threads is subsequently released, causing the web material to pucker or fold in the areas that contain the adhered elastic threads. In some applications, it is desired to provide areas of relative inelasticity in the elastic composite structure. To create these distinct regions, adhesive is applied to some areas of the web material and omitted from others. The elastic threads are cut in the adhesive-free areas by a cutting unit such as a rotary knife unit, and the cut ends of the elastic thread snap back to the adjoining adhesive areas.

The use of adhesives to bond the elastic threads within an elastic composite structure presents a number of disadvantages in both the end product and manufacturing method, including costs associated with the consumable material and undesirable tactile properties of the end product (e.g., stiffness). While thermal or ultrasonic welding techniques have been proposed as alternatives for bonding and/or cutting elastic threads within an elastic composite structure, known ultrasonic techniques for severing elastic threads tend to create cuts or slits in the web material, which reduce web tension in the severed part of the web and create an undesirable hole in the end product. Another problem associated with cutting the elastic threads is that the cut ends of elastic have a tendency to retract beyond the desired boundary of the elasticized area and land at a position somewhere within the elasticized area. This results in an incomplete elastic pattern and poor aesthetic and functional characteristics in the end product.

Accordingly, there is a need for an improved apparatus and method for fabricating an elastic composite structure of an absorbent sanitary product that maintains tension in the elastic strands within the elasticized areas of the product and does not cut the web materials in areas of relative inelasticity. It would further be desirable for such an apparatus and method to eliminate or minimize the use of consumable adhesives to secure the elastic threads to the facing web layers.

BRIEF DESCRIPTION OF THE INVENTION

In accordance with one aspect of the invention, a bonding apparatus is disclosed for manufacturing an elastic composite structure having at least one elastic thread secured between a pair of facing web layers. The bonding apparatus includes a rotary anvil having a face with weld pattern comprising at least one anchoring region and at least one deactivating region. The at least one anchoring region includes a plurality of anchoring welds constructed to form anchoring bonds that fuse the pair of facing web layers together and anchor the at least one elastic thread in position relative to the pair of facing web layers. The at least one deactivating region includes a break bar constructed to sever the at least one elastic thread.

In accordance with another aspect of the invention, a method of manufacturing an elastic composite structure includes positioning a tensioned elastic thread between a first web layer and a second web layer and fusing the first web layer to the second web layer to form an anchored zone comprising a plurality of discrete anchoring bonds that fuse the first web layer to the second web layer and anchor the tensioned elastic thread therebetween. The method also includes cutting the tensioned elastic thread to form a deactivated zone of the elastic composite structure that is free of the tensioned elastic thread, the deactivated zone positioned between adjacent portions of the anchored zone. The method further includes fusing the first web layer to the second web layer within the deactivated zone.

In accordance with another aspect of the invention, an elastic composite structure includes a tensioned elastic thread, a first web layer positioned on a first side of the tensioned elastic thread, a second web layer positioned on a second side of the tensioned elastic thread, and a pattern of bonds that fuses the first web layer to the second web layer. The pattern of bonds includes a deactivated zone that includes at least one bond of the pattern of bond, a cut end of a first portion of the tensioned elastic thread, and a cut end of a second portion of the tensioned elastic thread. The deactivated zone is free of the tensioned elastic thread. The pattern of bonds also includes an anchored zone bounding opposing ends of the deactivated zone. The anchored zone includes a first plurality of bonds of the pattern of bonds that anchor the first portion of the tensioned elastic thread to the first and second web layers and a second plurality of bonds of the pattern of bonds that anchor the second portion of the tensioned elastic thread to the first and second web layers.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings:

FIG. 4 is a detailed view of a portion of the bonding apparatus of FIG. 3 illustrating the horn aligned with an anchoring weld on the rotary anvil, according to one embodiment of the invention.

FIG. 5 is a detailed view of a portion of the bonding apparatus of FIG. 3 illustrating the horn aligned with a break bar on the rotary anvil, according to one embodiment of the invention.

FIG. 10A is a detailed view of a portion of the rotary anvil of FIG. 10.

FIG. 12 is a flattened representation of an exemplary anvil pattern usable to manufacture one of the elastic composite structures of FIG. 9, according to another embodiment of the invention.

FIG. 13 is a top view of a portion of a continuous elastic composite structure manufactured using the rotary anvil of FIG. 12, according to an embodiment of the invention.

FIG. 14 is a flattened representation of an exemplary anvil pattern usable to manufacture the continuous elastic composite structure of FIG. 9, according to another embodiment of the invention.

FIG. 15 is a top view of a portion of a continuous elastic composite structure manufactured using the rotary anvil of FIG. 14, according to an embodiment of the invention.

DETAILED DESCRIPTION

Embodiments of the present invention provide for a method and apparatus for manufacturing an elastic composite structure that includes one or more activated or elasticized zones, where one or more tensioned elastic threads are anchored or secured in place relative to facing web layers, and one or more deactivated zone that are inelastic relative to the elasticized zone(s). The resulting elastic composite structure may be used in an absorbent sanitary product such as, for example, a diaper, disposable adult pant, or feminine care product. As one non-limiting example, the elastic composite structure described herein may be a waistband for a diaper that includes a deactivated zone in an area where the absorbent core is coupled to the waistband.

Figure 1:
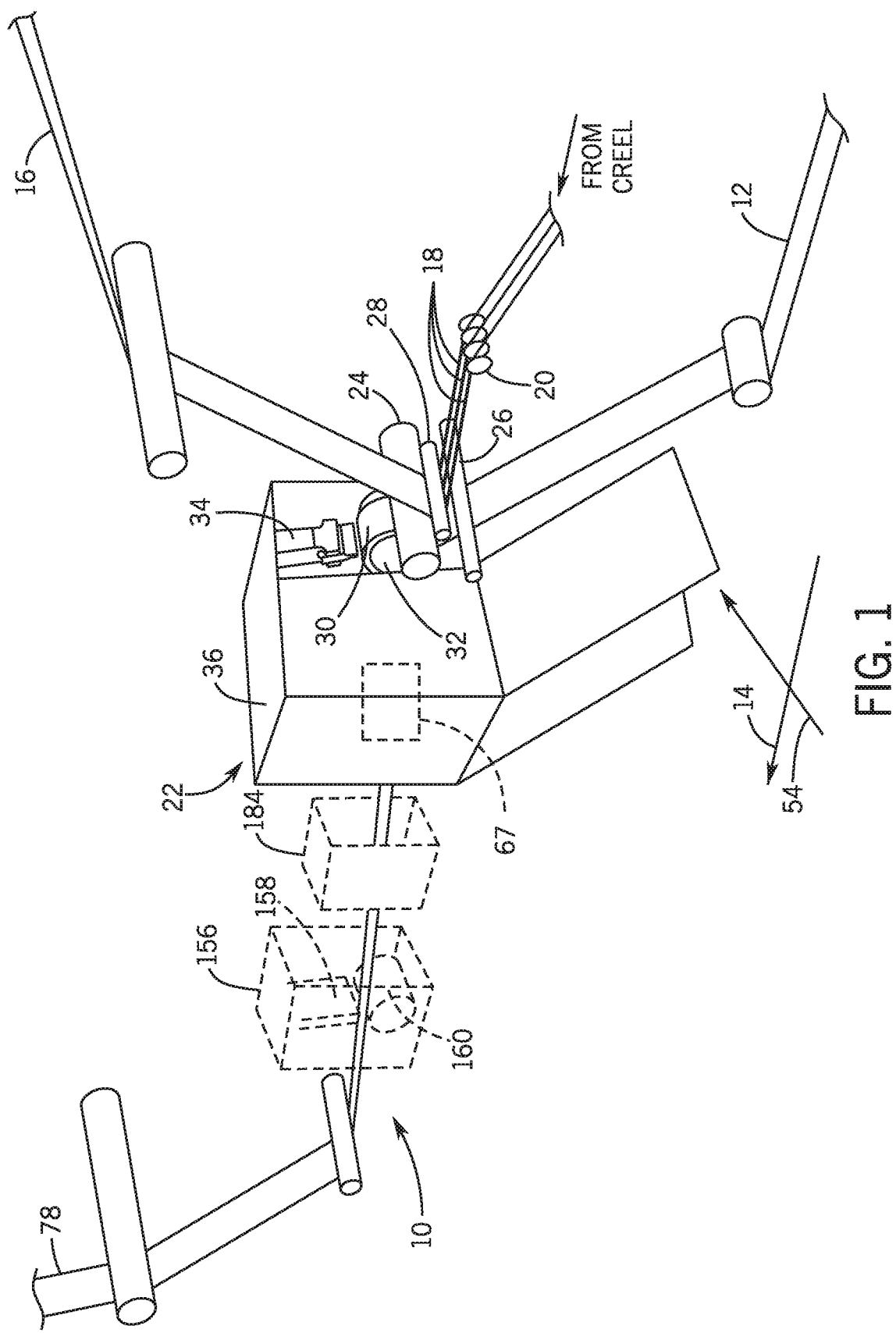
FIG. 1 is a schematic perspective view of a portion of a manufacturing line for fabricating an elastic composite structure.

Referring now to FIG. 1, a portion of an exemplary manufacturing line 10 is illustrated according to one embodiment of the invention. As shown, a first web layer 12 is fed in the machine direction 14. A second web layer 16 is similarly fed in the machine direction 14. First web layer 12 and second web layer 16 are materials capable of fusing to one another upon application of an applied energy that causes one or both of the webs 12, 16 to soften or melt and join together without the use of an intermediate layer of adhesive material such as glue. The facing pair of web layers 12, 16 may be the same type of material or different materials according to alternative embodiments. As non-limiting examples, first and second web layers 12, 16 may include nonwoven materials, woven materials, films, foams, and/or composites or laminates of any of these material types.

One or more elastic threads 18 are positioned between the first and second web layers 12, 16. While the below description refers to elastic threads in the plural form, it is to be understood that the methods described herein may be used to manufacture an elastic composite structure that includes a single elastic thread or any number of multiple elastic threads. The elastic threads 18 travel in the machine direction 14 under tension from a creel assembly (not shown) or similar device. The elastic threads 18 may be composed of any suitable elastic material including, for example, sheets, strands or ribbons of thermoplastic elastomers, natural or synthetic rubber, or LYCRA, as non-limiting examples. Each elastic thread 18 may be provided in the form of an individual elastomeric strand or be a manufactured multifilament product that includes many individual elastomeric filaments joined together, such as by a dry-spinning manufacturing process, to form a single, coalesced elastic thread 18.

Elastic threads 18 may have any suitable cross-sectional shape that facilitates formation of an elastic composite structure having desired elasticity, visual aesthetic, and manufacturability. As non-limiting examples, elastic threads 18 may have a cross-sectional shape that is round, rectangular, square, or irregular as may be the case where each elastic thread 18 is a multifilament product.

While first web layer 12 and second web layer 16 are depicted in FIG. 1 and described herein as physically separate components, it is contemplated that alternative embodiments may utilize a unitary web structure that is folded to capture the elastic threads 18 between upper and lower layers of the unitary web structure. In such an embodiment, the portion of the unitary structure positioned below the elastic threads 18 would be referred to as the first web layer 12 and the portion of the unitary structure positioned above the elastic threads 18 would be referred to as the second web layer 16.

Manufacturing line 10 includes one or more feeding assemblies 20 such as guide rollers that are employed to accurately position and (optionally) tension the elastic threads 18 as they travel in the machine direction 14 toward a bonding apparatus 22. Immediately upstream of the bonding apparatus 22 are one or more assemblies that feed and guide the first and second web layers 12, 16 and the elastic threads 18 into the bonding apparatus 22. In the illustrated embodiment, these feeding assemblies include an upper roller 24, a lower roller 26, and a strand guide roller 28 that guide a combined assembly 30 that includes the first web layer 12, the second web layer 16, and the elastic threads 18 into the bonding apparatus 22. It is contemplated that rollers 24, 26, 28 may be replaced with other known types of feeding assemblies and/or replaced by a single roller unit or other known type of feeding assembly in an alternative embodiment.

Bonding apparatus 22 may be any known ultrasonic welding system in alternative embodiments, including, as non-limiting examples, a rotary ultrasonic welding system or a blade ultrasonic welding system. In the illustrated embodiment, bonding apparatus 22 includes a rotary anvil 32 and an ultrasonic fixed blade horn 34, also known as a sonotrode, which cooperate with each other to bond (i.e., fuse) the first web layer 12 to the second web layer 16. Alternative embodiments may include multiple fixed blade horns or one or more rotary horns. During the bonding process the elastic threads 18 are secured or anchored in position relative to the first and second web layers 12, 16 as described in detail below.

Bonding apparatus 22 also includes one or more frames 36 that support and/or house a motor (not shown) that drives the ultrasonic horn 34, a vibration control unit (not shown) that ultrasonically energizes the horn 34 and causes the horn 34 to vibrate, and a second motor (not shown) that drives the anvil 32. The horn 34 and anvil 32 are positioned in a spaced relationship relative to one another to facilitate ultrasonically bonding the first and second web layers 12, 16 to one another while the elastic threads 18 are held in tension in the space between the horn 34 and anvil 32. During the bonding process, the first and second web layers 12, 16 are exposed to an ultrasonic emission from the horn 34 that increases the vibration of the particles in the first and second web layers 12, 16. The ultrasonic emission or energy is concentrated at specific bond points where frictional heat fuses the first and second web layers 12, 16 together without the need for consumable adhesives. While bonding apparatus 22 is described herein as an ultrasonic bonding assembly that ultrasonically fuses first web layer 12 to second web layer 16, it is contemplated that the techniques described herein may be extended to any other known welding or bonding techniques that fuse together two or more material layers without the use of adhesive, including sonic, thermal, or pressure bonding techniques and various other forms of welding known in the industry.

Figure 2:
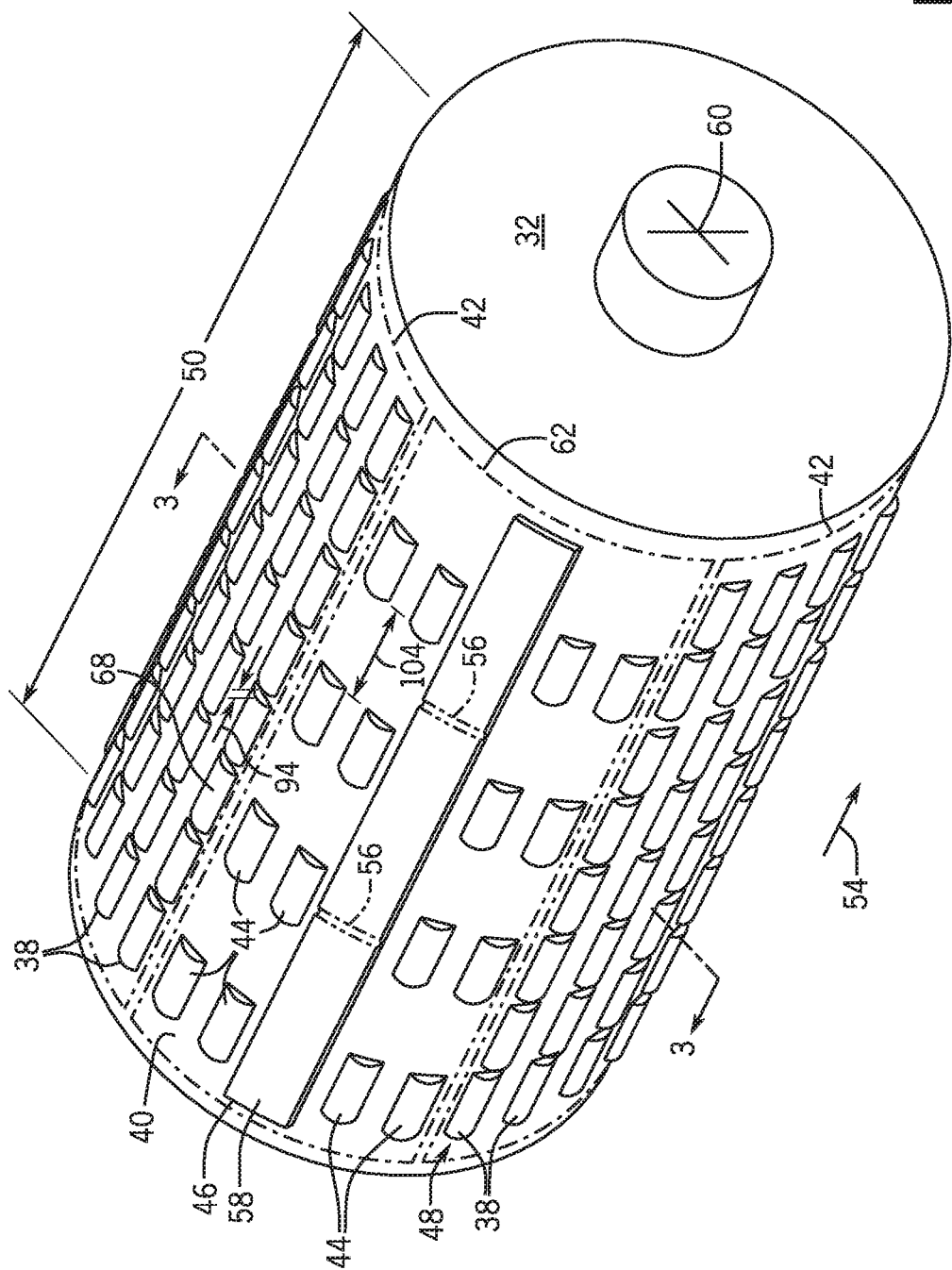
FIG. 2 is a schematic perspective view of a rotary anvil usable with the manufacturing line of FIG. 1, according to one embodiment of the invention.

Referring now to FIG. 2, anvil is illustrated according to one embodiment of the invention. As shown, the anvil 32 of includes an arrangement of discrete projections or welds 38 that extend outward from the anvil face 40. These welds 38 are constructed to (A) fuse first and second web layers 12, 16 together and (B) restrain or anchor the elastic threads 18 in position relative to the first and second web layers 12, 16 in the manufactured elastic composite structure. As described in more detail below, anchoring welds 38 are designed so that an elastic thread 18 that passes between two adjacent anchoring welds 38 on the face 40 of anvil 32 is anchored in position relative to the first and second web layers 12, 16 by frictional resistance that prevents the elastic thread 18 from sliding through the pair of resulting bonds. The location of anchoring welds 38 define anchoring regions 42 of the anvil 32.

Anvil 32 also includes one or more additional projections that are referred to herein as laminating welds 44. Similar to the restraining or anchoring welds 38, laminating welds 44 fuse first and second web layers 12, 16 to one another. Laminating welds 44 differ from anchoring welds 38 because they do not anchor the elastic threads 18 in position relative to the first and second web layers 12, 16.

Anvil 32 also includes one or more edges or break bars 46 that extends outward from the anvil face 40. Each break bar 46 is configured to break the elastic threads 18 when the tensioned elastic threads 18 pass between the horn 34 and anvil 32 without cutting or perforating the first web layer 12 or the second web layer 16. The pressure or pinching force exerted on a given elastic thread 18 as it passes between the horn 34 and the break bar 46 imparts a stress on the elastic thread 18 that breaks the elastic thread 18. In a preferred embodiment, break bar(s) 46 are constructed so that they do not bond the first and second web layers 12, 16 to one another. In an alternative embodiment, break bar(s) 46 form a bond between the first and second web layers 12, 16 that has a geometry that mirrors that of the working surface of the respective break bar 46. Together the anchoring welds 38, laminating weld(s) 44, and break bar(s) 46 define a pattern of projections 48 or weld pattern that extends outward from the face 40 of the anvil 32.

In the illustrated embodiment, break bar 46 has a length equal or substantially equal to the overall length 50 of the pattern of projections 48. In alternative embodiments, each break bar 46 may be sized to span only a subportion of the overall anvil length 50, as described in further detail below. Optionally, break bar(s) 46 may include one or more grooves 56 (shown in phantom) that are recessed within the working surface 58 of the break bar(s) 46. In yet other embodiments, the break bar 46 is constructed of a series of discrete but closely spaced projections or pinching welds, so called because the close spacing of two adjacent pinching welds functions as a pinch point that severs an elastic thread 18 that passes through the adjacent pinching welds during the bonding process. Break bar(s) 46 may be linear and oriented parallel to the rotational axis 60 of the anvil 32, as shown, oriented at an angle relative to the rotational axis 60, or have any alternative geometrical configuration determined based on design specifications to achieve the desired result of cutting an elastic thread 18.

The location of break bar 46 defines a deactivating region 62 of the anvil 32, which corresponds to a region of deactivated or broken elastic threads in the manufactured elastic composite structure and is referred to hereafter as a deactivated zone. One or more laminating weld(s) 44 are also located within the deactivating region 62 of the anvil 32. In the illustrated embodiment, deactivating region 62 includes one break bar 46 with laminating welds 44 positioned on both sides of the break bar 46. Alternative embodiments may include multiple break bars 46 within a given deactivating region 62 with laminating welds 44 positioned on one or both sides of each break bar 46. Laminating welds 44 may be omitted entirely from the deactivating region 62 in yet other embodiments.

The particular size, shape, and general arrangement of anchoring welds 38, laminating welds 44, and break bar 46, as well as the total number of welds 38, 44 and break bar(s) 46 illustrated in FIG. 2, are intended to depict a representative and non-limiting example of an overall pattern of projections 48 on anvil 32. Alternative embodiments may include any number of welds 38, 44 and break bar(s) 46 arranged in any number of alternative configurations to achieve a desired pattern of bonds on the end product. The respective working surfaces of anchoring welds 38 and laminating welds 44 may be configured to form bonds of similar size and shape, or bonds of different size and/or shape in alternative embodiments. As non-limiting examples, respective land surfaces of anchoring welds 38 and laminating welds 44 may be circular, rectangular, crescent shaped, or have irregular shapes that may be selected to form a desired overall pattern on the end product. As explained above, the resulting pattern of bonds will include one or more anchored zones, which fix one or more elastic threads 18 under tension in position relative to the first and second web layers 12, 16, and one or more deactivated regions or zones, which are free of tensioned elastic threads 18. Being free of tensioned elastic threads 18, these deactivated zones define areas of relative inelasticity in the resulting elastic composite structure.

In a preferred embodiment the anchoring welds 38, laminating welds 44, and break bar(s) 46 are formed on anvil 32 using a machining process that removes bulk material from the anvil 32 to create the desired raised pattern of projections 48 relative to the face 40 of the anvil 32. Alternatively, anchoring welds 38, laminating welds 44, and/or break bar(s) 46 may be provided on one or more inserts that are mechanically coupled to the face 40 of the anvil 32.

Figure 3:
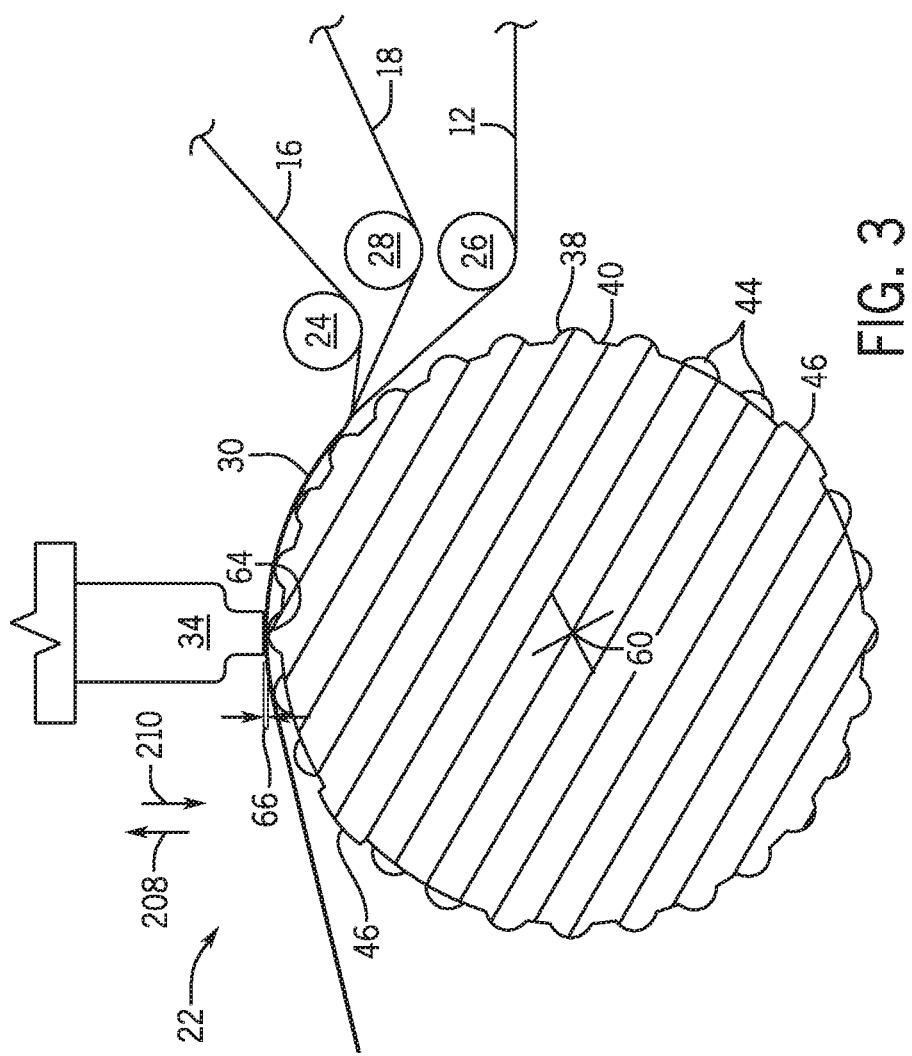
FIG. 3 is a schematic cross-sectional view of a bonding apparatus that includes the rotary anvil of FIG. 2 and is usable with the manufacturing line of FIG. 1, according to one embodiment of the invention.

Referring now to FIG. 3, the working surface 64 of the horn 34 has a smooth or substantially smooth surface contour in one non-limiting embodiment. Alternatively, working surface 64 may include an arrangement of projections that mate or align with the pattern of projections 48 on the anvil 32 to further facilitate fusing the first web layer 12 to the second web layer 16 and securing the elastic threads 18 in position relative to the first and second web layers 12, 16.

During the manufacturing process, the first and second web layers 12, 16 are positioned between the face 40 of the anvil 32 and the working surface 64 of the horn 34 as shown in FIG. 3. Elastic threads 18 are positioned between the first and second web layers 12, 16 in a tensioned state. As generally shown in FIG. 3 and in further detail in FIG. 4, the position of horn 34 is controlled to maintain a nip gap 66 between the working surface 64 of horn 34 and the land surfaces 68, 70 of the anchoring welds 38 and laminating welds 44, respectively. The size of the nip gap 66 is determined based on parameters of the manufacturing process to facilitate bonding between the first and second web layers 12, 16. Bonding apparatus 22 may include any known positioning means 67 that exerts a force on at least one of the horn 34 and anvil 32 to maintain a desired nip gap 66 between the horn 34 and anvil 32. Positioning means 67 may be an air pressure assembly (not shown) or a mechanical camshaft (not shown) as non-limiting examples.

Anchoring welds 38 may have a planar working surface, planar side surfaces, or some mixture of curved and straight working and side surfaces in alternative embodiments. In the embodiment illustrated in FIG. 4, the land surface 68 of anchoring weld 38 has an arced or curved surface profile. This curved profile permits the first and second weld layers 12, 16 to slip relative to the face 40 of the anvil 32 during the bonding process and thus allows the velocity at which the combined assembly 30 including tensioned elastic strands 18 and first and second web layers 12, 16 is advanced toward the bonding apparatus 22 to be increased or decreased relative to the rotational velocity of the anvil 32. When the combined web/thread assembly 30 is advanced at a velocity greater than the velocity of the anvil 32, the resulting bonds are spaced apart by a distance greater than the radial spacing between of adjacent welds 38, 44 on the anvil face 40. Similarly, slowing the feed rate of the combined web/thread assembly 30 relative to the velocity of the anvil 32 will result in bonds that are spaced apart by a distance less than the radial spacing between of adjacent welds 38, 44 on the anvil face 40. The velocity mismatch or differential between web speed and anvil velocity can be controlled to accommodate size changes in the end product. As a result, the bonding of an elastic composite for one size diaper may be carried out with little or no slip, while the bonding of an elastic composite for a larger or smaller diaper may be carried out with a larger amount of slip. A manufacturing line 10 outfitted with anvil 32 thus provides for dynamic size changing without having to change the tooling set-up of the manufacturing line 10, as the same anvil 32 can be used to manufacture multiple sizes of elastic composite structures for use in different sized products.

FIG. 5 is a detailed view of the relationship between the horn 34 and a break bar 46 on the anvil 32. In the embodiment shown, break bar 46 has straight side surfaces 72 and a curved working surface 58, to permit slip to occur between the anvil 32 and first and second web layers 12, 16 in a manner similar to that described above with respect to anchoring weld 38. Alternatively, the entire working surface 58 of break bar 46 may have a continuous arced profile similar to that of anchoring weld 38 of FIG. 4. In yet other embodiments, working surface 58 may be flat or planar, side surfaces 72 may be curved, or break bar 46 may be configured with any other geometric profile that accomplishes the intended function of cutting the elastic threads 18 and, optionally, fusing the first and second web layers 12, 16.

As shown in FIG. 5, the working surface 64 of horn 34 is spaced apart from the working surface 58 of break bar(s) 46 by a nip gap 76. In one embodiment, nip gap 76 is equal or substantially equal to the nip gap 66 between working surface 64 of horn 34 and the land surfaces 68, 70 of the anchoring and laminating welds 38, 44. In alternative embodiments where it is desired that break bar(s) 46 form a bond between the first and second web layers 12, 16 by virtue of the geometry of the break bar(s) 46, size of the nip gap 76, or a combination thereof.

Figure 6:
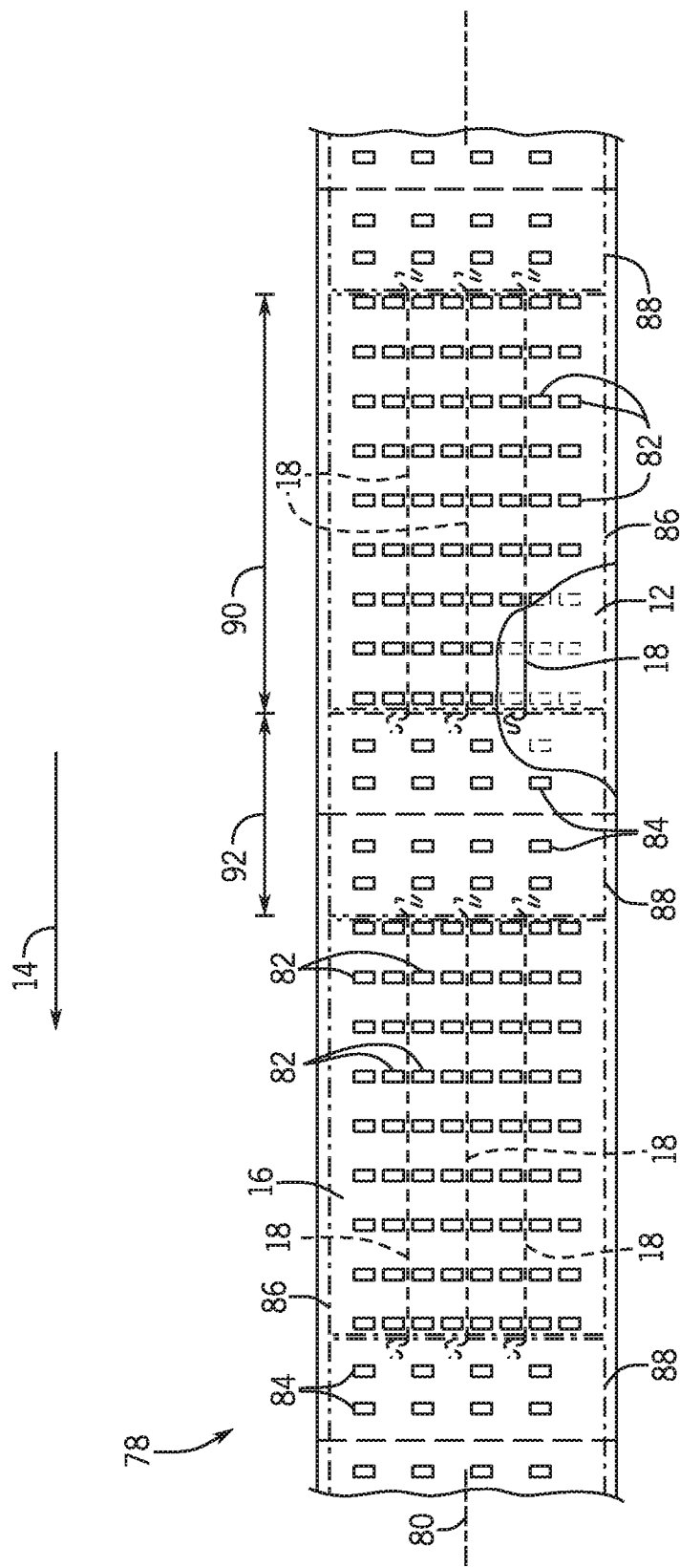
FIG. 6 is a top view of a portion of a continuous elastic composite structure manufactured using the rotary anvil of FIG. 2, according to one embodiment of the invention.

FIG. 6 illustrates a portion of an elastic composite structure 78 formed using the anvil 32 with pattern of projections 48 shown in FIG. 2. The elastic composite structure 78 is illustrated in an elongated state with elastic threads 18 stretched to a point where the first web layer 12 and second web layer 16 are flat or substantially flat. Elastic threads 18 are located between the first and second web layers 12, 16 are oriented along a longitudinal axis 80 of the elastic composite structure 78. While the illustrated embodiment includes three (3) elastic threads 18 it is contemplated that alternative embodiments may include a single elastic thread 18 or any number of multiple elastic threads 18 based on design specifications of the end product.

The first and second web layers 12, 16 are fused together by anchoring bonds 82 at locations where the anchoring welds 38 on anvil 32 (FIG. 2) communicate with web layers 12, 16 and by laminating bonds 84 at locations where the laminating welds 44 on anvil 32 (FIG. 2) communicate with web layers 12, 16. The break bar(s) 46 of anvil 32 break the elastic threads 18, causing them to snap back toward the nearest anchoring bonds 82. When the elastic composite structure 78 is permitted to relax, the elastic threads 18 will attempt to swell or expand to return to their non-tensioned or relaxed state. As the elastic threads 18 expand, frictional forces restrain or anchor the threads 18 between adjacent anchoring bonds 82 and the first and second web layers 12, 16. The result is an elastic composite structure 78 that includes one or more elasticized or anchored regions or zones 86 corresponding to the anchoring region 86 of anvil 32 and one or more non-elasticized or deactivated zone 88 corresponding to the deactivating region 62 of anvil 32. The length 90 of the anchored zone(s) 86 and the length 92 of the deactivated zone(s) 88 is defined by control of the rotational speed of the anvil 32 relative to the feed rate of the combined web/thread assembly 30 during the bonding process and anvil geometry.

Figure 7:
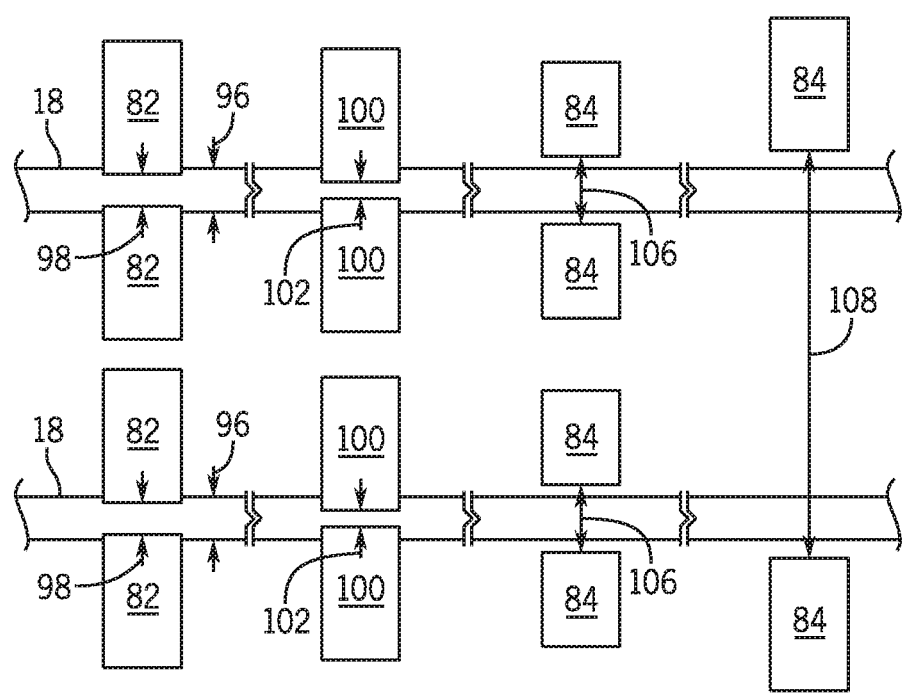
FIG. 7 is a schematic top view illustrating the spaced relationship between a non-tensioned elastic thread, a pair of anchoring bonds, a pair of pinching bonds, and laminating bonds, according to various embodiments of the invention.

Referring now to FIG. 7 together with FIG. 2 as appropriate, in one embodiment the proximal edges of adjacent anchoring welds 38 are spaced apart from one another by a distance 94 that is less than the strand diameter 96 of a given elastic thread 18 in its non-tensioned state. As used herein the phrase "strand diameter" refers to the smallest measurable cross-sectional width of the elastic thread 18 in its non-tensioned state. In embodiments where a given elastic thread 18 is a monofilament structure, the strand diameter is the minor diameter or smallest measurable width of the monofilament structure in its non-tensioned state. In embodiments where a given elastic thread 18 is a multifilament structure, the phrase "strand diameter" refers to the smallest distance between opposite edges of an outline that generally defines the irregular cross-sectional area. The adjacent anchoring welds 38 on anvil 32 form a pair of adjacent anchoring bonds 82 that will act to secure or anchor the elastic thread 18 because the distance 98 between the proximal edges of the adjacent anchoring bonds 82 is smaller than the strand diameter 96 of the non-tensioned elastic thread 18, as shown in FIG. 7.

In embodiments where break bar 46 is configured with discrete pinching welds, adjacent pinching welds will form a pair of adjacent pinching bonds 100 having proximal edges spaced apart by a distance 102 that is smaller than the strand diameter 96 and the distance 98 between adjacent anchoring bonds 82.

In embodiments where the anvil 32 of FIG. 2 includes multiple adjacent laminating welds 44, the adjacent welds 44 are spaced apart at a distance 104 that forms a pair of adjacent laminating bonds 84 having proximal edges spaced apart either by (A) a distance 106 that is greater than the strand diameter 96 of a single non-tensioned elastic thread 18, as illustrated by laminating bonds 84A in FIG. 7, or (B) a distance 108 that is greater than the summed total of the strand diameters 96 of two or more non-tensioned elastic threads 18, as illustrated by laminating bonds 84B.

Figure 8:
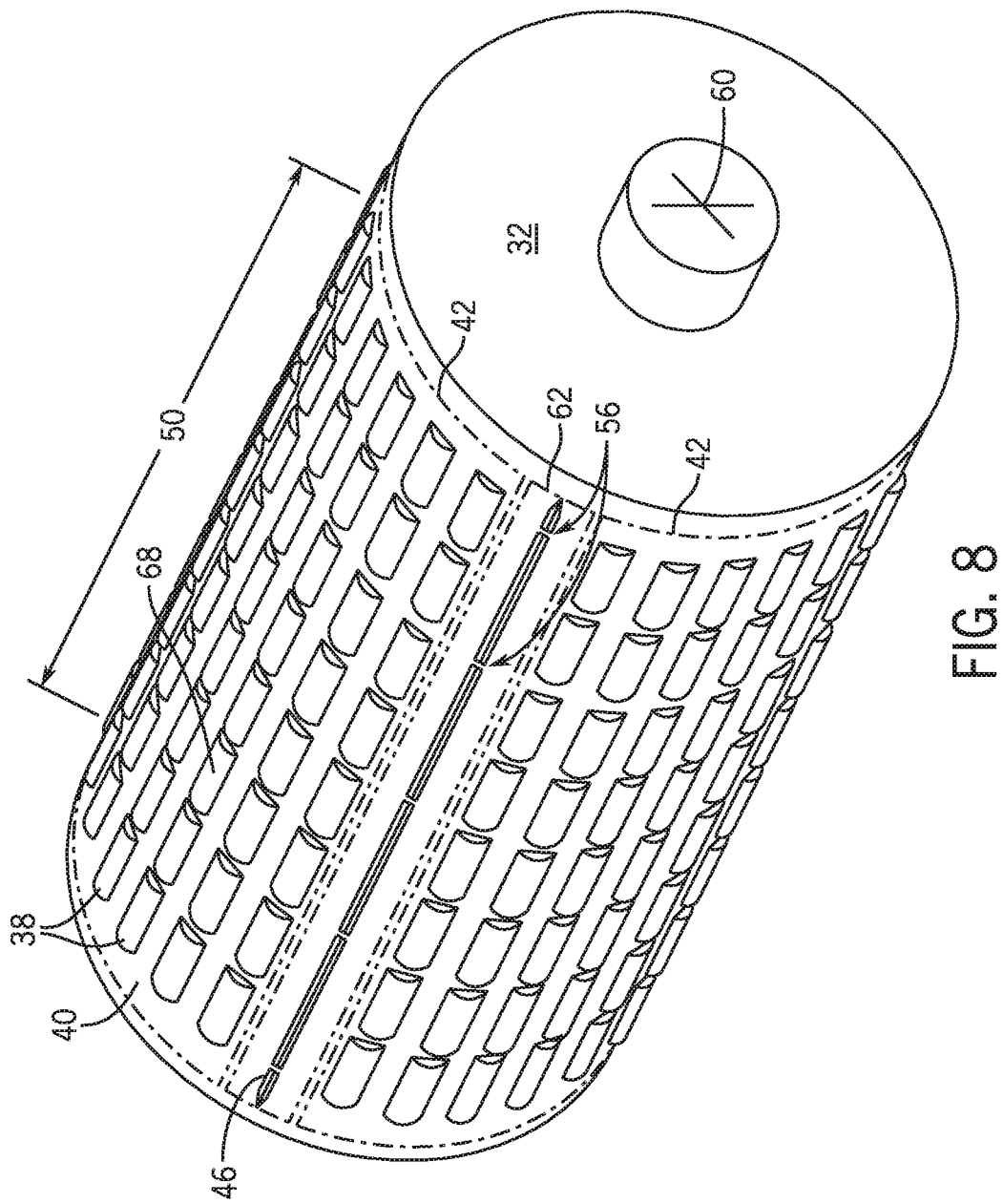
FIG. 8 is a schematic perspective view of a rotary anvil usable with the manufacturing line of FIG. 1, according to another embodiment of the invention.

FIG. 8 illustrates anvil 32 according to an alternative embodiment of the invention. Anvil 32 includes a pattern of projections 110 that differs from the pattern of projections 48 described with respect to FIG. 2 in that it includes a narrower break bar 46 and does not include laminating welds 44. In such an embodiment, the resulting elastic composite structure would include anchored zones similar to the anchored zone 86 shown in FIG. 6 and a deactivated zone that includes a bond line formed by break bar 46 but does not include any laminating bonds. In one embodiment an adhesive may be used to couple the first and second web layers 12, 16 together within the deactivated zone. Alternatively, laminating bonds similar to the laminating bonds 84 of FIG. 6 may be formed within the deactivated zone using a second anvil unit positioned downstream from anvil 32, as described in more detail below.

In the embodiment described with respect to FIGS. 2-8, the anchored zones 86 and deactivated zones 88 span similar widths of the resulting elastic composite structure 78 in the cross-machine direction 54 as a result of the particular configuration of the break bar(s) 46, laminating weld(s) 44 (when used), and anchoring welds 38 on the anvil 32. FIGS. 10, 12, 14, and 16 depict alternative anvil projection patterns that may be used with the bonding apparatus 22 of FIG. 1 to form deactivated zones 88 that span only a portion of the overall width of the resulting elastic composite structure. These alternative projection patterns may be used to manufacture continuous elastic composite structures such as the front waist panel 112 and rear waist panel 114 illustrated in FIG. 9. As shown, front and rear waist panels 112, 114 include anchored zones 86 that contain multiple anchoring bonds that anchor elastic threads 18 and deactivated zones 88 that define attachment locations for respective absorbent cores 116 of a disposable diaper or pant and may include laminating bonds in some embodiments. Lines 118 represent product cut lines. Each of FIGS. 10, 12, 14, and 16 is to be understood as illustrating one exemplary and non-limiting pattern of projections for manufacturing waist panels 112, 114. The concepts described herein may be extended to manufacture an end product with one or more anchored zones and one or more deactivated zones using an anvil with an alternative pattern of projections than those described relative to FIGS. 10, 12, 14, and 16. Thus, it is contemplated that the pattern of projections on anvil may be modified from those shown herein to create an elastic composite structure that includes one or more anchored zone(s) and one or more deactivated zone(s) that vary in size and/or position relative to the embodiments specifically depicted herein.

Figure 9:
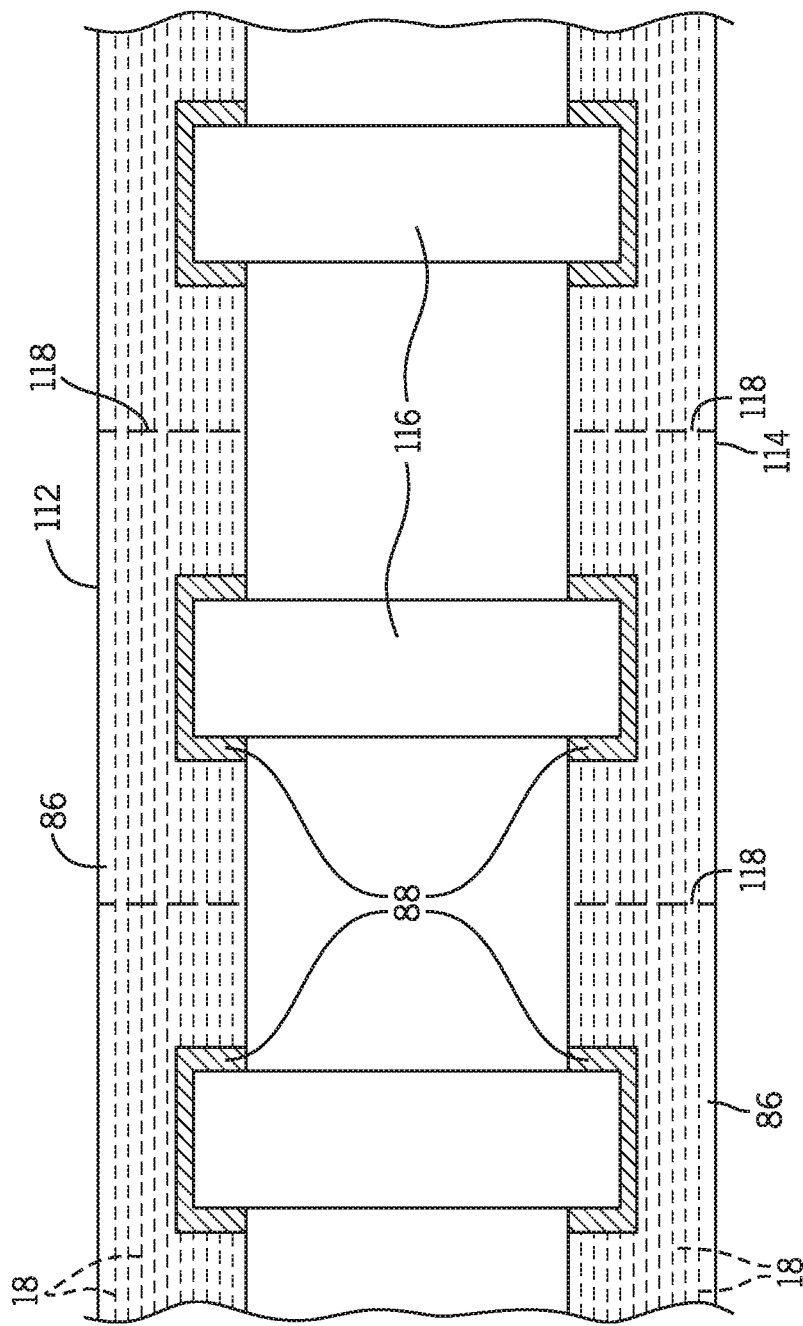
FIG. 9 is a top view of a plurality of non-segmented absorbent sanitary products that includes a continuous elastic composite structure manufactured using the manufacturing line of FIG. 1, according to one embodiment of the invention.
Figure 10:
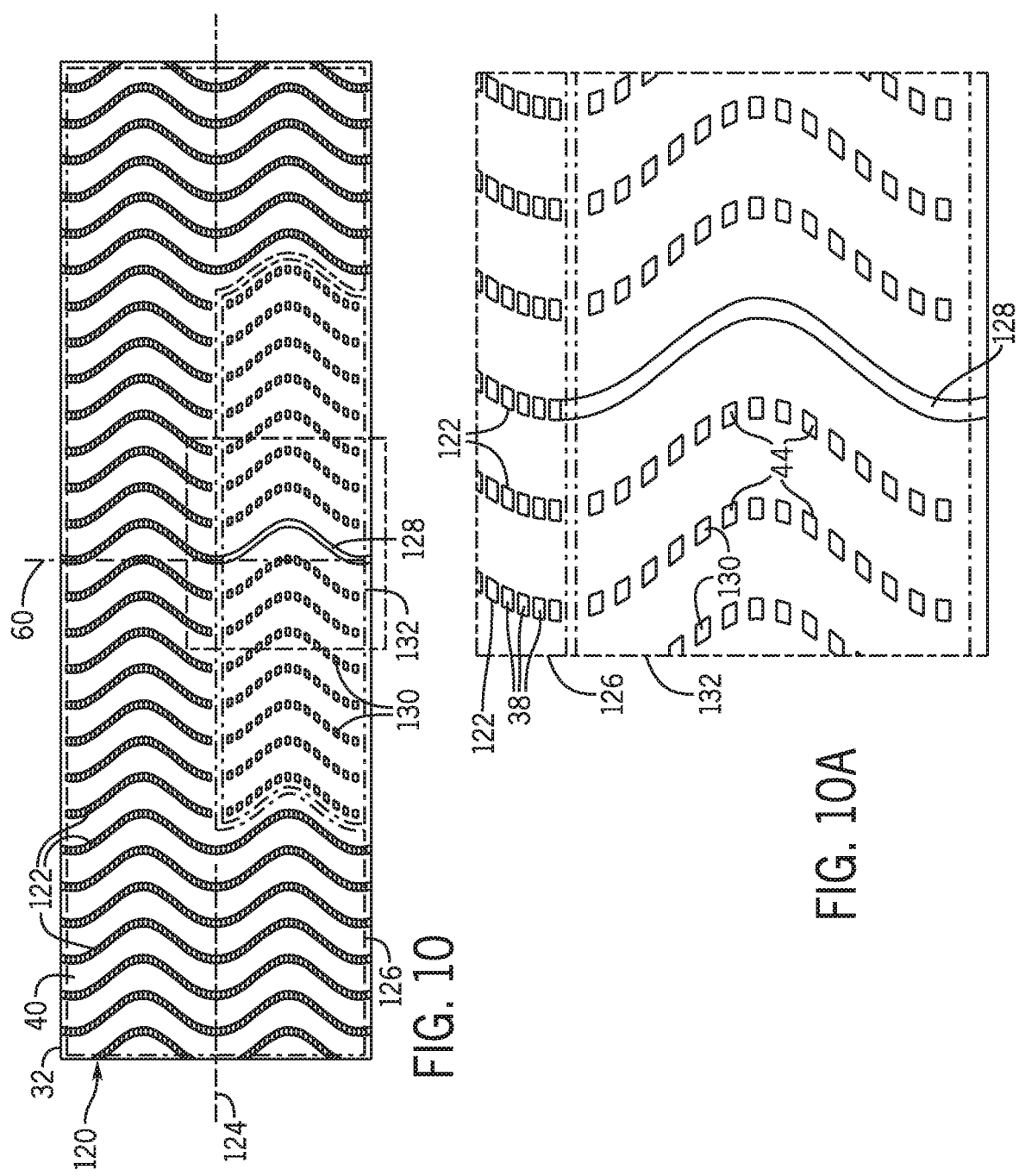
FIG. 10 is a flattened representation of an exemplary anvil pattern usable to manufacture the continuous elastic composite structure of FIG. 9, according to one embodiment of the invention.

FIG. 10 is a flattened representation of the circumferential face 40 of anvil 32 according to an embodiment where anvil 32 includes a pattern of projections 120 that form the deactivated zones 88 and anchored zones 86 of FIG. 9. The pattern of projections 120 includes multiple anchoring weld lines 122 that are spaced apart from one another along the circumferential axis 124 of the anvil face 40. The anchoring weld lines 122 define an anchoring region 126 of the projection pattern 120. The pattern of projections 120 also includes a break bar 128 and plurality of laminating weld lines 130 that collectively define a deactivating region 132.

As shown in the detailed view provided in FIG. 10A, each of the anchoring weld lines 122 contains a plurality of discrete anchoring welds 38. Likewise, each of the laminating weld lines 130 includes a plurality of discrete laminating welds 44, which are spaced apart from one another at a distance greater than that of the anchoring welds 38. In alternative embodiments, each laminating weld line 130 may consist of a single laminating weld 44 or the laminating weld lines 130 may be omitted altogether. Break bar 128 may be formed having a continuous working surface as shown, or include one or more grooves similar to grooves 56 of FIG. 2.

In the embodiment shown, break bar 128, laminating weld lines 130, and anchoring weld lines 122 have a similar sinusoidal geometry that results in an overall sinusoidal pattern across the anvil face 40. In this embodiment, break bar 128 is constructed to fuse the first and second web layers 12, 16 and sever the elastic thread(s) 18 that pass between the break bar 128 and horn 34 (FIG. 1) during the bonding process. In an alternative embodiment, one or more of the laminating weld lines 130 immediately adjacent the leading and trailing edges of the deactivating region 62 may be omitted. Break bar 128, laminating weld lines 130, and anchoring weld lines 122 may be straight lines, curved lines, or otherwise arranged to create a continuous and repeating overall pattern on the end product in alternative embodiments.

Figure 11:
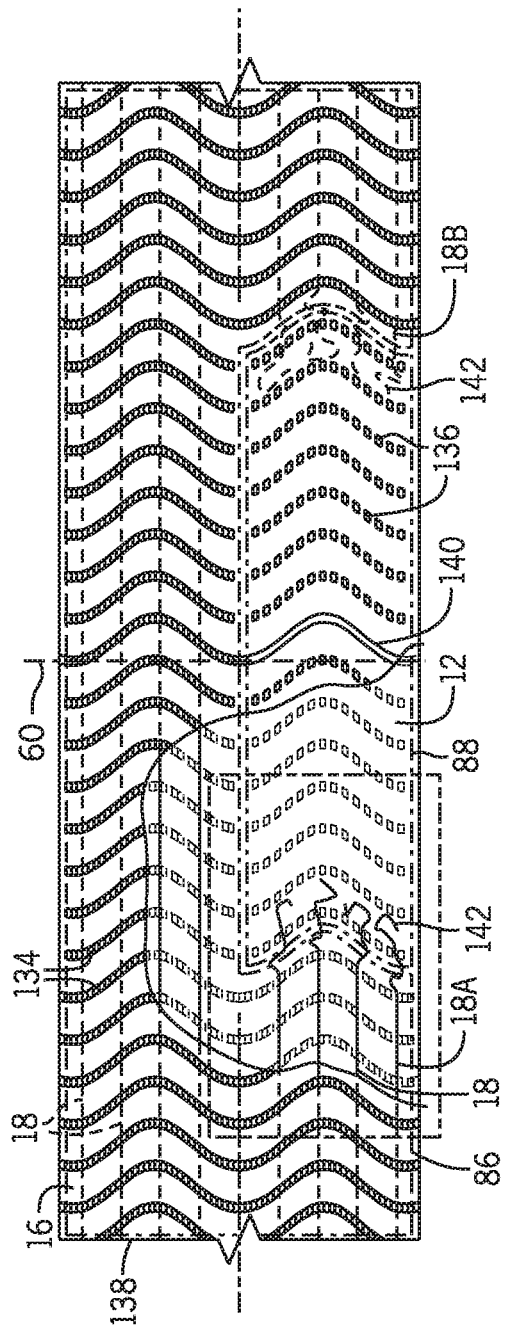
FIG. 11 is a top view of a portion of a continuous elastic composite structure manufactured using the rotary anvil of FIG. 10, according to an embodiment of the invention.
Figure 11A:
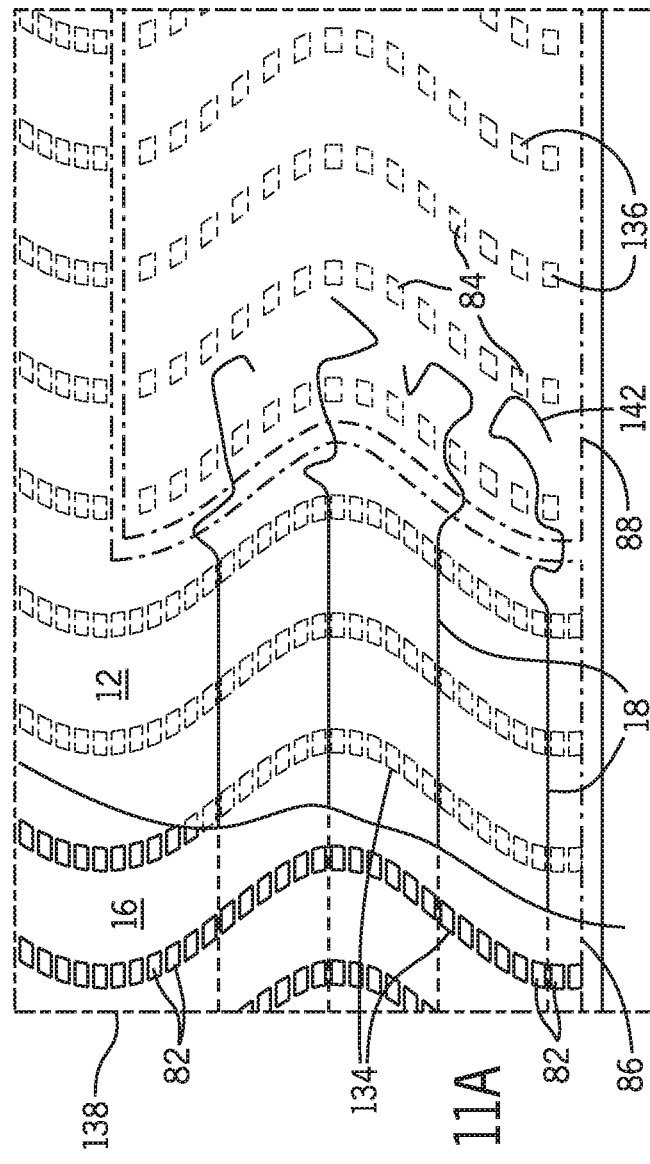
FIG. 11A is a detailed view of a portion of the elastic composite structure of FIG. 11.

As shown in FIG. 11, the bonding process creates an overall pattern of anchoring bond lines 134 and laminating bond lines 136 on the resulting elastic composite structure 138 that mirrors the geometry of anchoring weld lines 122 and laminating weld lines 130 within the pattern of projections 120 of FIG. 10. Thus, in an embodiment where the weld lines 122, 130 are sinusoidal, the resulting bond lines 134, 136 have a similar sinusoidal pattern. Alternative bond patterns on elastic composite structure 138 may be achieved by varying the geometry of the corresponding weld lines 122, 130 on the anvil 32. In the illustrated embodiment a continuous bond line 140 is formed by break bar 128, which severs the elastic threads 18. The severed or cut ends 142 of the elastic threads 18 snap back toward the nearest anchoring bond lines 134, which secures the two segmented portions 18A, 18B of a given cut elastic thread 18 under tension and in position relative to the first and second web layers 12, 16. In an alternative embodiment, break bar 128 may be configured to sever the elastic threads 18 without fusing first and second web layers 12, 16. The anchoring bond lines 134 also bond the first and second web layers 12, 16 together and define the anchored zones 86. The first and second web layers 12, 16 are bonded together within the deactivated zones 88 by the continuous bond line 140 formed by break bar 128 and by laminating bond lines 136 formed by the laminating weld lines 130 on anvil 32. Similar to the embodiments described above, the anchoring bond lines 134 collectively define anchored zone 86 on the elastic composite structure 138. A deactivated zone 88 is defined the laminating bond lines 136 and continuous bond line 140 (when formed).

FIG. 12 illustrates a pattern of projections 144 formed on anvil 32 according to an alternative embodiment of the invention. Pattern of projections 144 includes anchoring weld lines 122, which that are arranged in a similar manner as those included in the pattern of projections 120 of FIG. 10 and include discrete anchoring welds similar to anchoring welds 38 in FIG. 10A. Pattern of projections 144 also includes a pair of break bars 128, one positioned at the leading edge of the deactivating region 132 and the other positioned at the trailing edge of the deactivating region 132. A series of laminating weld lines 130 are positioned between break bars 128, each of which include discrete laminating welds similar to laminating welds 44 of FIG. 10A.

The pattern of projections 144 creates an elastic composite structure 138 that includes the pattern of bonds depicted in FIG. 13. Since each break bar 128 severs the elastic threads 18 as the elastic threads 18 pass over it, the use of two break bars 128 produces two cut points in a given elastic thread 18 that passes through the deactivating region 132 of the anvil 32, resulting in a severed elastic thread portion 146 for each of those elastic threads 18. These severed elastic portions 146 are retained within the deactivated zone 88 of the resulting elastic composite structure 138 as shown in FIG. 13.

FIG. 14 depicts an alternative pattern of projections 148 on anvil 32 according to another embodiment of the invention. The anchoring region 126 includes anchoring weld lines 122 similar to those of FIGS. 10 and 10. Deactivating region 132 includes an alternating pattern of anchoring weld lines 122 and break bars 128. In one embodiment, the break bars 128 are constructed so that they do not fuse first and second web layers 12, 16. During the bonding process each elastic thread 18 that passes through the deactivating region 132 of the anvil 32 is cut by each of the break bars 128. The result is the elastic composite structure 138 shown in FIG. 15, which includes a series of severed elastic thread portions 146 corresponding to each elastic thread 18 that passes through the deactivating region 132. These severed elastic thread portions 146 are anchored in place by anchoring bond lines 134 within the anchored zone 86.

Figure 16:
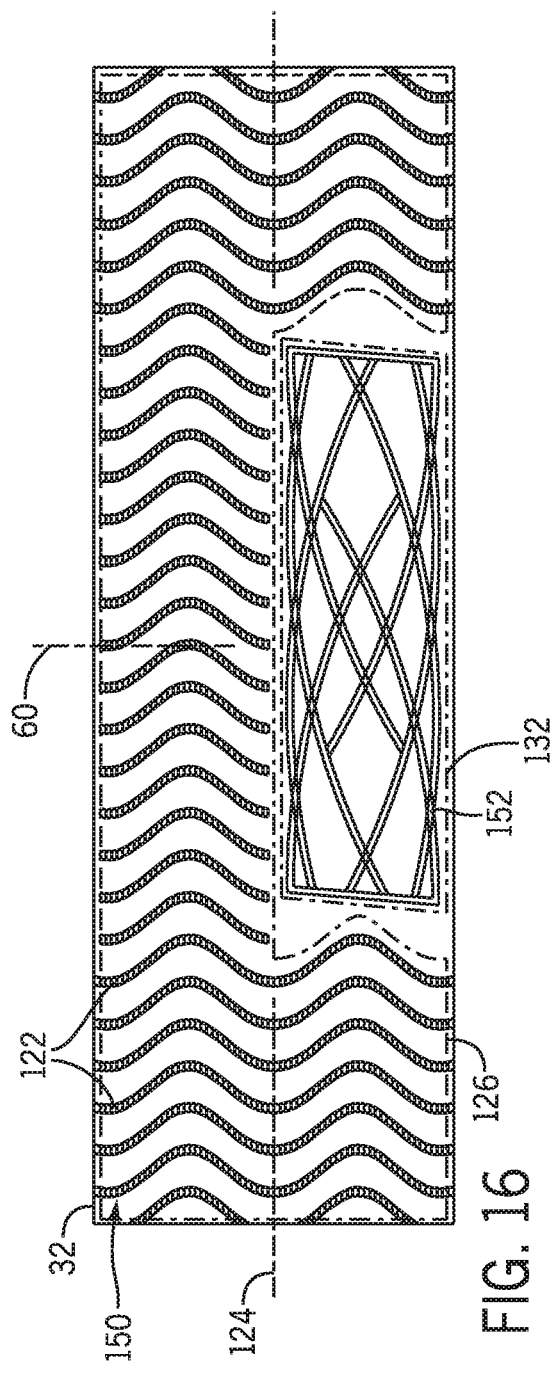
FIG. 16 is a flattened representation of an exemplary anvil pattern usable to manufacture the continuous elastic composite structure of FIG. 9, according to yet another embodiment of the invention.
Figure 17:
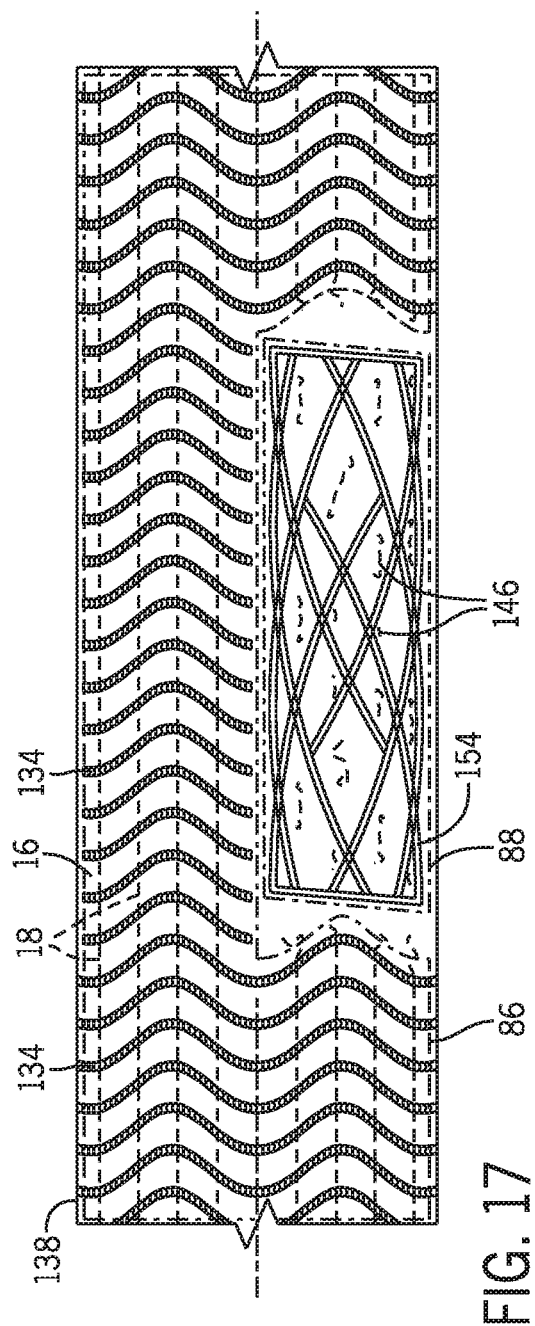
FIG. 17 is a top view of a portion of a continuous elastic composite structure manufactured using the rotary anvil of FIG. 16, according to an embodiment of the invention.

Yet another alternative pattern of projections 150 is shown in FIG. 16. In this embodiment, the deactivating region 132 of the pattern 150 includes a continuous weld pattern 152 that simultaneously cuts the elastic threads 18 and forms a corresponding unbroken bond pattern 154 or geometric design on the resulting elastic composite structure 138, as shown in FIG. 17. Each elastic thread 18 that passes between the weld pattern 152 and horn 34 (FIG. 1) during the bonding process may be cut one or multiple times based on geometry of the weld pattern 152. In the embodiment shown, the weld pattern 152 cuts each of the affected elastic threads 18 two or more times, resulting in numerous severed elastic thread portions 146 that are contained within the bond pattern 154 in the elastic composite structure 138. The continuous weld pattern 152 shown in FIG. 16 is to be understood as only one example of a weld pattern geometry that may be implemented within the pattern of projections 150. In alternative embodiments, pattern of projections 150 may include a continuous weld pattern 152 that forms any desired pattern, shape, design, logo, or the like on the resulting elastic composite structure 138.

The bond patterns depicted on the elastic composite structures 138 in FIGS. 11, 13, 15, and 17 are described above as being formed using a single anvil 32 with a pattern of projections that defines the location and boundaries of the anchored and deactivated zones on the end product. Alternatively, a similar end product may be manufactured using two or more anvils that each include a portion of the overall pattern of projections. In such an embodiment, the multiple anvils would be positioned adjacent one another in the cross-machine direction 54 (i.e., the direction perpendicular to the machine direction 14) and configured to rotate simultaneously about a common axis of rotation.

In an alternative embodiment, the first and second web layers 12, 16 are fused together using multiple bonding apparatuses positioned in series in the machine direction 14. With reference to FIG. 1, a first bonding apparatus 22 is outfitted with a first anvil 32 that includes a pattern of projections that forms a first portion of the overall bond pattern and one or more horns 34. A second bonding apparatus 156 is positioned downstream from the first bonding apparatus 22 in the machine direction 14. Second bonding apparatus 156 includes a second horn 158 and a second anvil 160, which includes a second pattern of projections that completes the overall bond pattern. Second bonding apparatus 156 may include multiple horns and/or multiple anvils in alternative embodiments.

Figure 18:
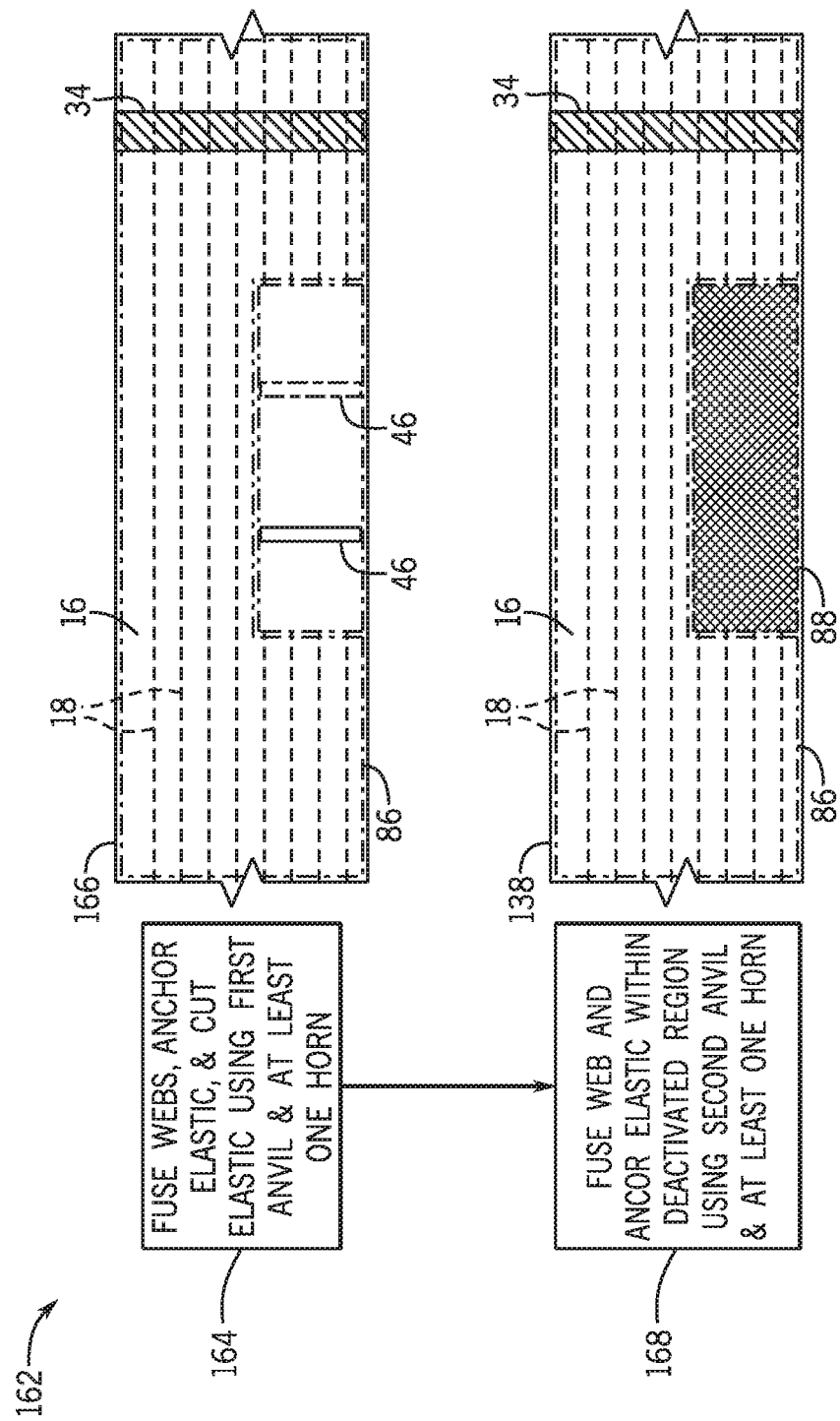
FIG. 18 depicts a technique for manufacturing an elastic composite structure, according to another embodiment of the invention.

FIG. 18 depicts an exemplary manufacturing method 162 that utilizes this two-stage anvil arrangement. Method 162 begins at step 164 by operating the first anvil 32 in combination with the horn 34 to bond the first and second web layers 12, 16 together. Anvil 32 includes one or more break bar(s) 46 that cut or sever the elastic threads 18. The resulting intermediate product 166 is shown in FIG. 18 with the position of the horn 34 and break bar(s) 46 overlaid atop the intermediate product 166 for reference. The intermediate product 166 includes an anchored zone 86 and a deactivated zone 88, which at this point in the manufacturing process do not include any laminating bonds 84. The anchored zone 86 include anchoring bond lines 134, similar to those described relative to FIGS. 11, 13, 15, and 17, which are formed by anchoring weld lines 122 and corresponding anchoring welds 38 similar to any of those described with respect to FIGS. 2, 10, 12, 14, and 16.

Method 162 continues at step 168 by fusing the first and second web layers 12, 16 within the resulting deactivated zone(s) 88 via a pattern of laminating welds or laminating weld lines similar to any of those described with respect to FIGS. 2, 10, 12, 14, and 16. The result is an elastic composite structure 138 that includes one or more anchored zones 86 and one or more deactivated zones 88.

Figure 19:
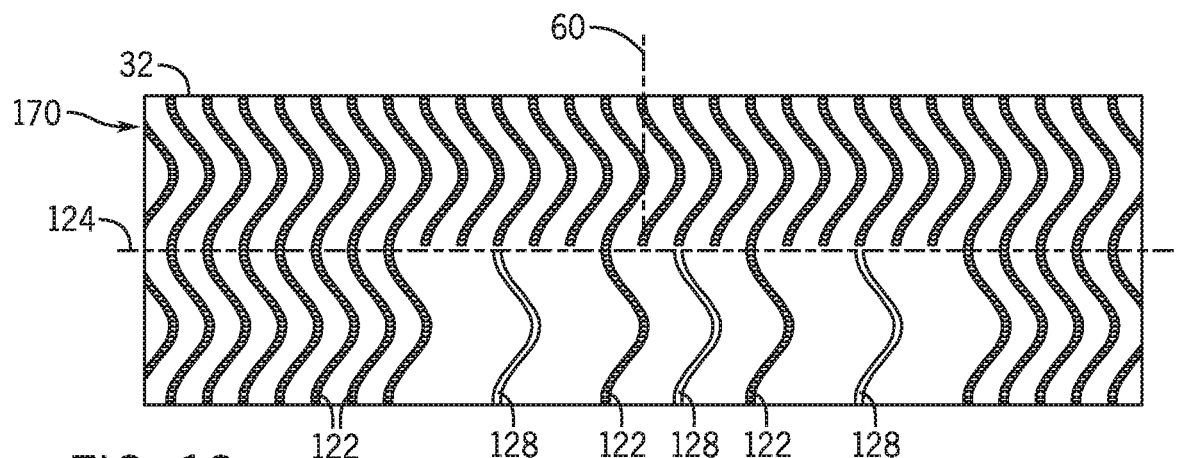
FIG. 19 is a flattened representation of an exemplary anvil pattern usable to manufacture an elastic composite structure in accordance with the technique of FIG. 18, according to one embodiment of the invention.
Figure 20:
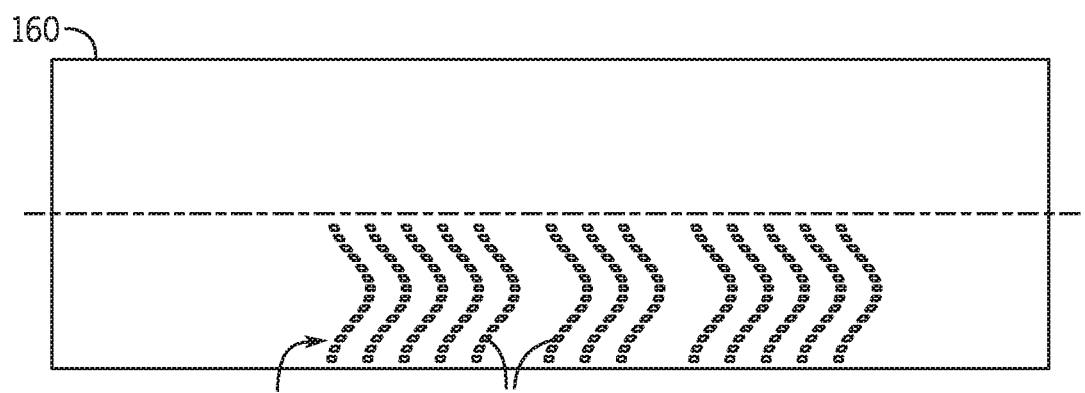
FIG. 20 is a flattened representation of an exemplary anvil pattern usable to manufacture an elastic composite structure in accordance with the technique of FIG. 18, according to one embodiment of the invention.
Figure 21:
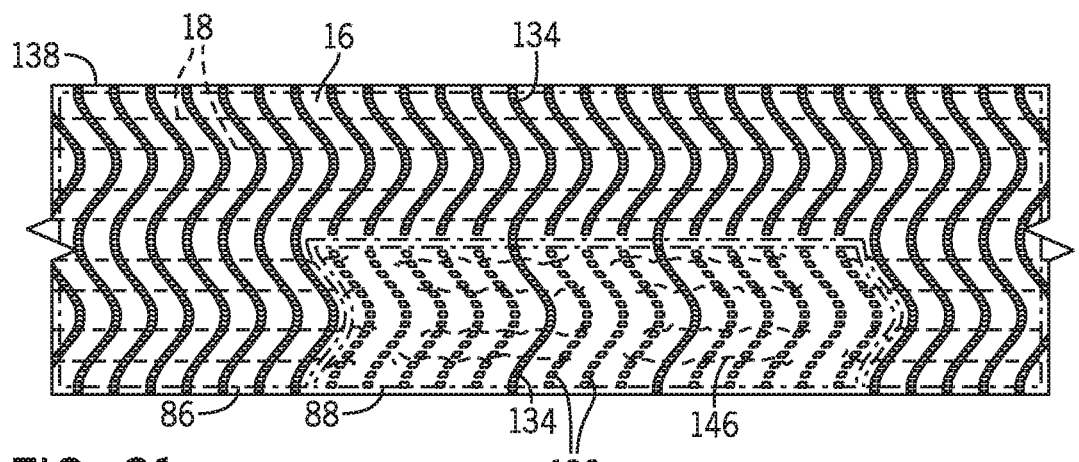
FIG. 21 is a top view of a portion of an elastic composite structure manufactured using the rotary anvils of FIGS. 19 and 20, according to an embodiment of the invention.

FIGS. 19 and 20 show flattened representations of the respective circumferential faces of the first anvil 32 and the second anvil 160, according to one embodiment of the invention. First anvil 32 includes a first pattern of projections 170 with anchoring weld lines 122 and break bars 128. Second anvil 160 includes a second pattern of projections 172 that includes a series of laminating weld lines 130. When anvils 32, 160 are operated in the manner described with respect to method 162 of FIG. 18, the first and second projection patterns 170, 172 form the elastic composite structure 138 shown in FIG. 21. In the illustrated embodiment, the break bars 128 shown in FIG. 19 are not configured to form bonds between first and second web layers 12, 16 of the elastic composite structure 138 (FIG. 21). In an alternative embodiment, the geometry of break bars 128 may be designed to form bond lines within the deactivated zone 88.

Figure 22:
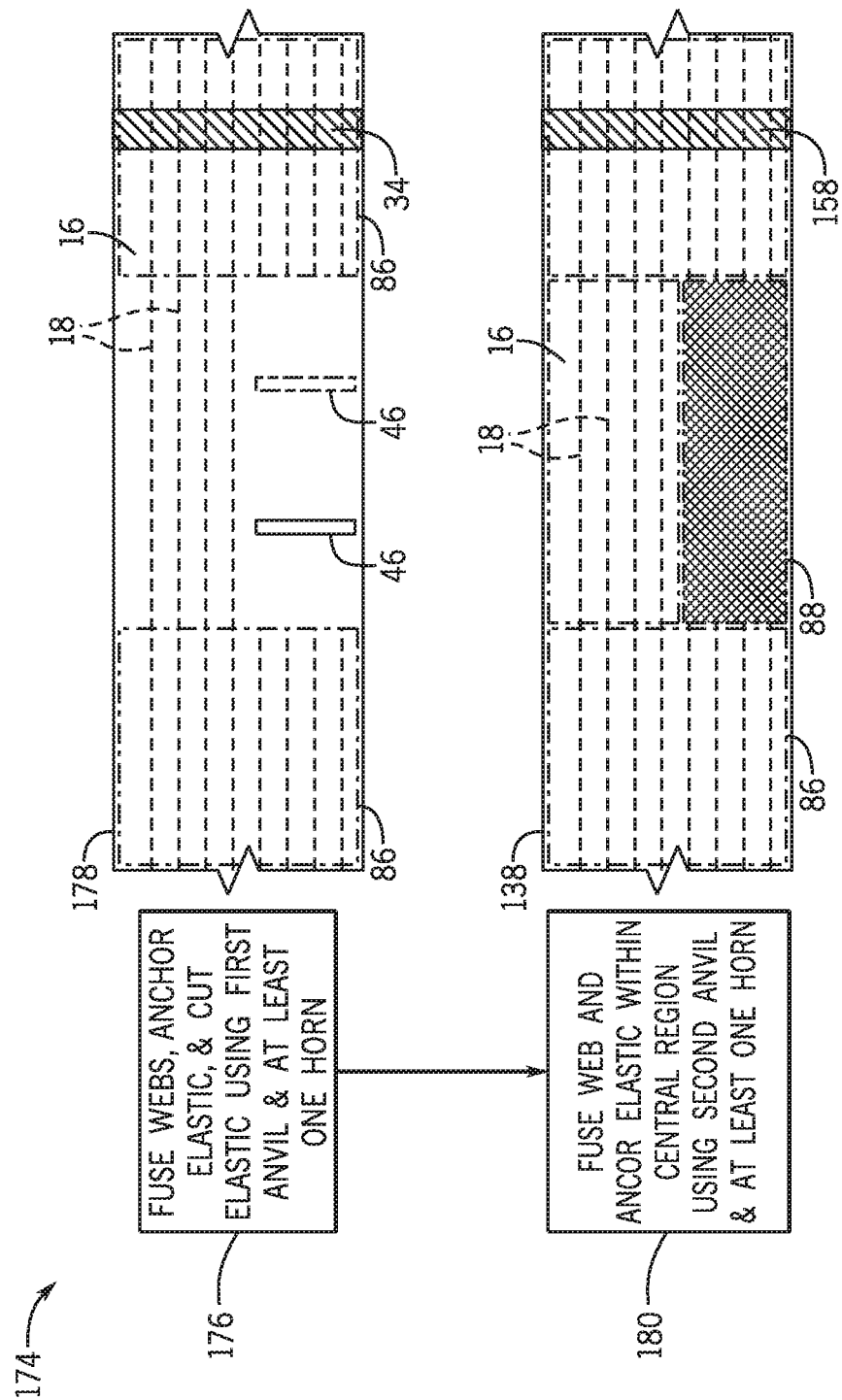
FIG. 22 depicts a technique for manufacturing an elastic composite structure, according to yet another embodiment of the invention.

An alternative two-stage bonding method 174 is illustrated in FIG. 22. Similar to method 162 of FIG. 18, technique 174 utilizes a pair of anvils 32, 160 arranged in series in the machine direction 14 to form the overall bond pattern. Methods 162, 174 differ from one another through the use of different patterns of projections on anvils 32, 160. During a first step 176 of method 174, a first portion of the overall bond pattern is formed using a first anvil 32 that includes a pattern of projections that forms intermediate product 178. As shown in FIG. 22, the intermediate product 178 includes discrete anchored zones 86 that span the width of the product 178. First anvil 32 also includes one or more break bar(s) 46 that sever the elastic and create one or more deactivated zones 88.

During the second step 180 of method 174, the overall bond pattern is completed using second anvil 160, which includes anchoring weld lines 122 in addition to one or more laminating weld lines 130. Second anvil 160 forms one or more laminating bonds 84 within the deactivated zones 88 and one or more additional anchored zones 86, resulting in the elastic composite structure 138.

Figure 23:
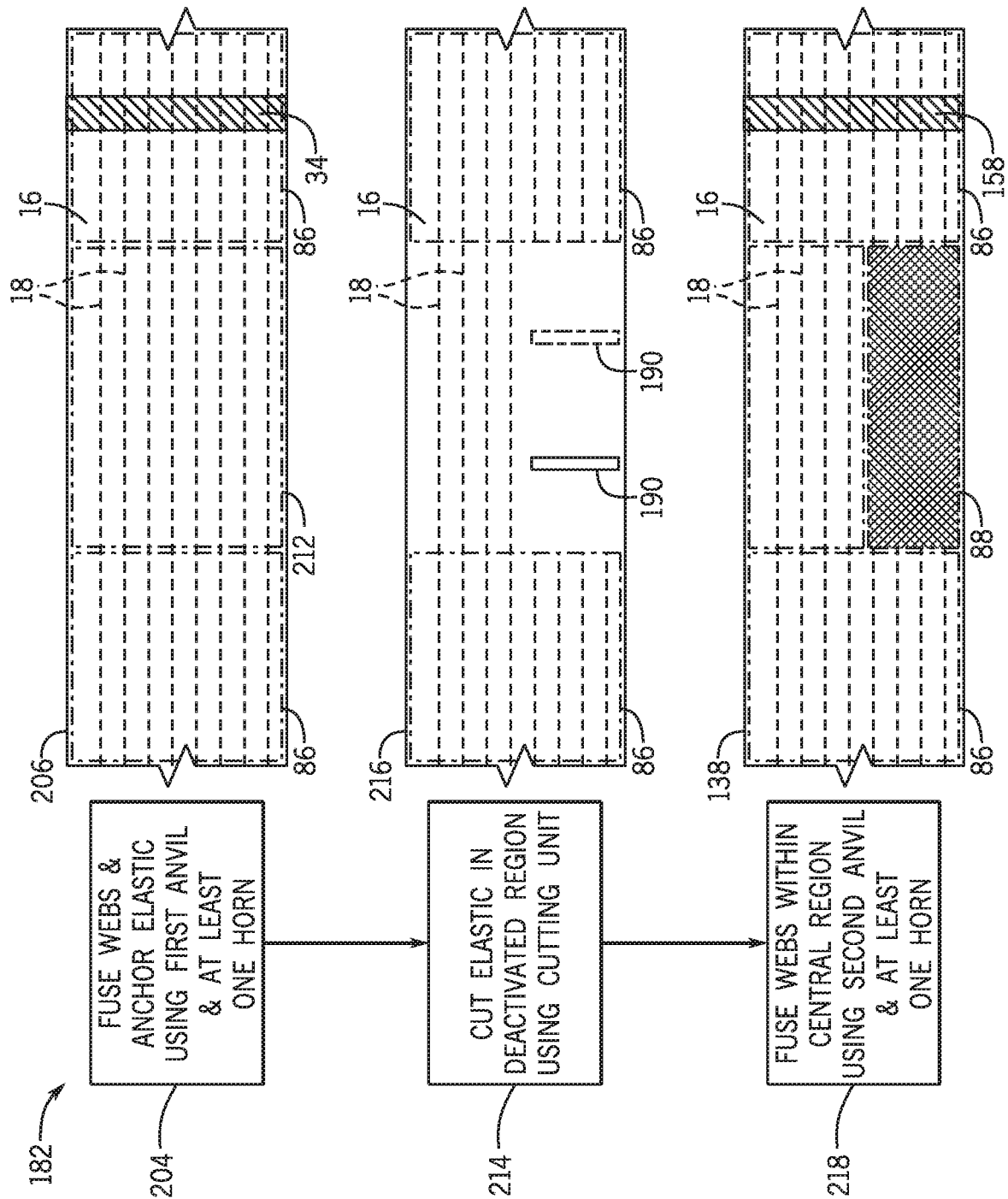
FIG. 23 depicts a technique for manufacturing an elastic composite structure, according to yet another embodiment of the invention.

Yet another alternative method 182 for forming elastic composite structure 138 is illustrated in FIG. 23. Method 182 utilizes a manufacturing line 10 that includes first anvil 32, a cutting unit 184 positioned downstream from the anvil 32 as shown in FIG. 1, and a second anvil 160 positioned downstream from cutting unit 184. A detailed view of a portion of cutting unit 184 is provided in FIG. 24, according to one embodiment of the invention. Cutting unit 184 includes a rotary knife roll 186 aligned with a rotary anvil 188. A knife 190 is positioned within an insert 192 on the rotary knife roll 186. An anvil insert 194 is inset within the rotary anvil 188. Cutting unit 184 may include a single knife 190 and corresponding anvil insert 194 or multiple knife 190/anvil insert 194 pairs spaced apart from one another around the respective faces of the knife unit 186 and rotary anvil 188. Each rotary knife roll 186 and its corresponding rotary anvil 188 are spaced apart at a distance that defines a nip gap 196 between the knife 190 and the working surface 198 of the anvil insert 194. In a preferred embodiment, the nip gap 196 is defined such that the force of the knife 190 on the anvil insert 194 is large enough to sever the elastic threads 18 without severing or creating slits in the first and second web layers 12, 16.

In the illustrated embodiment, the working surface 198 of the anvil insert 194 is sloped between its leading edge 200 and trailing edge 202. The sloped configuration of working surface 198 permits the size of the nip gap 196 to be adjusted by adjusting the phase or relative rotational position between the knife 190 and anvil insert 194. In alternative embodiments, working surface 198 may be flat, curved, or any other geometry to facilitate the desired cutting functionality. Anvil insert 194 may be omitted entirely in another embodiment. Cutting unit 184 is described herein as a crush cut unit. In other embodiments, cutting unit 184 may be replaced with alternative types of cutting units known in the art, including units having rotary or non-rotary configurations and laser systems.

Referring again to FIG. 23 in combination with FIGS. 1-3 as appropriate, method 182 begins at step 204 using first anvil 32 to form discrete anchored bond zones 86 on intermediate product 206. In one embodiment, anvil 32 includes a uniform pattern of anchoring welds 38 that extend around the circumferential face 40 of the anvil 32. Horn 34 oscillates up and down in the direction of arrows 208, 210 (FIG. 3) between a raised position and a lowered position during the bonding process. This oscillation may be carried out using a mechanical camshaft assembly coupled to the horn 34 or other known position control mechanism 67. When horn 34 is in its lowered position, anchoring bonds 82 are formed within the desired anchored bond zones 86. When horn 34 is in its raised position, horn 34 is moved out of communication with anvil 32 and a region 212 free of bonds is formed within the intermediate product 206. At step 214 the partially bonded intermediate product 206 passes through cutting unit 184, which severs one or more of the elastic threads 18 and forms one or more deactivated zones 88 in the resulting intermediate product 216. Intermediate product 216 passes through second anvil 160 at step 218, which includes a pattern of projections that includes anchoring weld lines and laminating weld lines that completes the bond pattern on the elastic composite structure 138.

Figure 25:
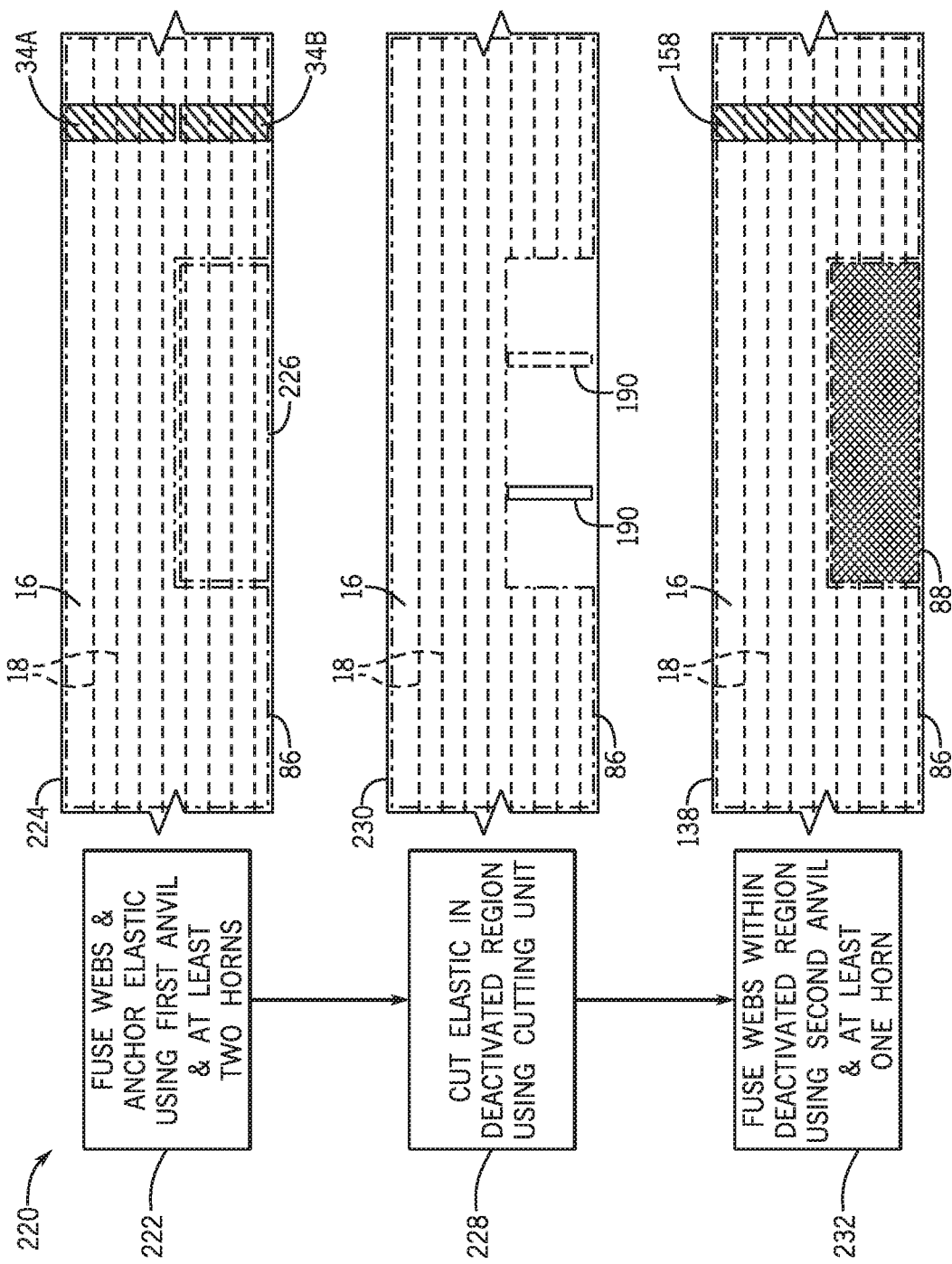
FIG. 25 depicts a technique for manufacturing an elastic composite structure, according to yet another embodiment of the invention.

FIG. 25 depicts an alternative method 220 for forming elastic composite structure 138 using the optional cutting unit 184 and dual bonding apparatus 22, 156 arrangement of FIG. 1. For this method 220, bonding apparatus 22 is outfitted with at least two horns 34A, 34B and an anvil 32 with a uniform pattern of anchoring welds 38 that spans the circumferential face 40 of the anvil 32. During the first step 222 of the method 220, an intermediate product 224 is formed by oscillating horn 34B between raised and lowered positions in a similar manner as described with respect to step 204 of method 182 (FIG. 22) to produce a region 226 free of bonds. At step 228, the knife 190 (or knives) severs one or more of the elastic threads 18 and forms one or more deactivated zones 88 in the resulting intermediate product 230. At step 232, the second anvil 160 forms one or more laminating bonds within the deactivated zone 88 to complete the elastic composite structure 138.

Beneficially, method 220 can be carried out to produce different sized end products without tooling changes by controlling time intervals in which the oscillating horn 34B is held in the raised and lowered positions during step 222 and controlling the web speed relative to the rotational speed of the second anvil 160 in step 232. More specifically, oscillating horn 34B would be retained in the raised position for a longer time interval for a larger sized product vs. a smaller sized product to produce a longer region 226 free of bonds. During step 232, the relative web-to-anvil speed would be controlled to form a pattern of laminating bonds that spans the resulting bond free region 226 by a desired amount.

Figure 24:
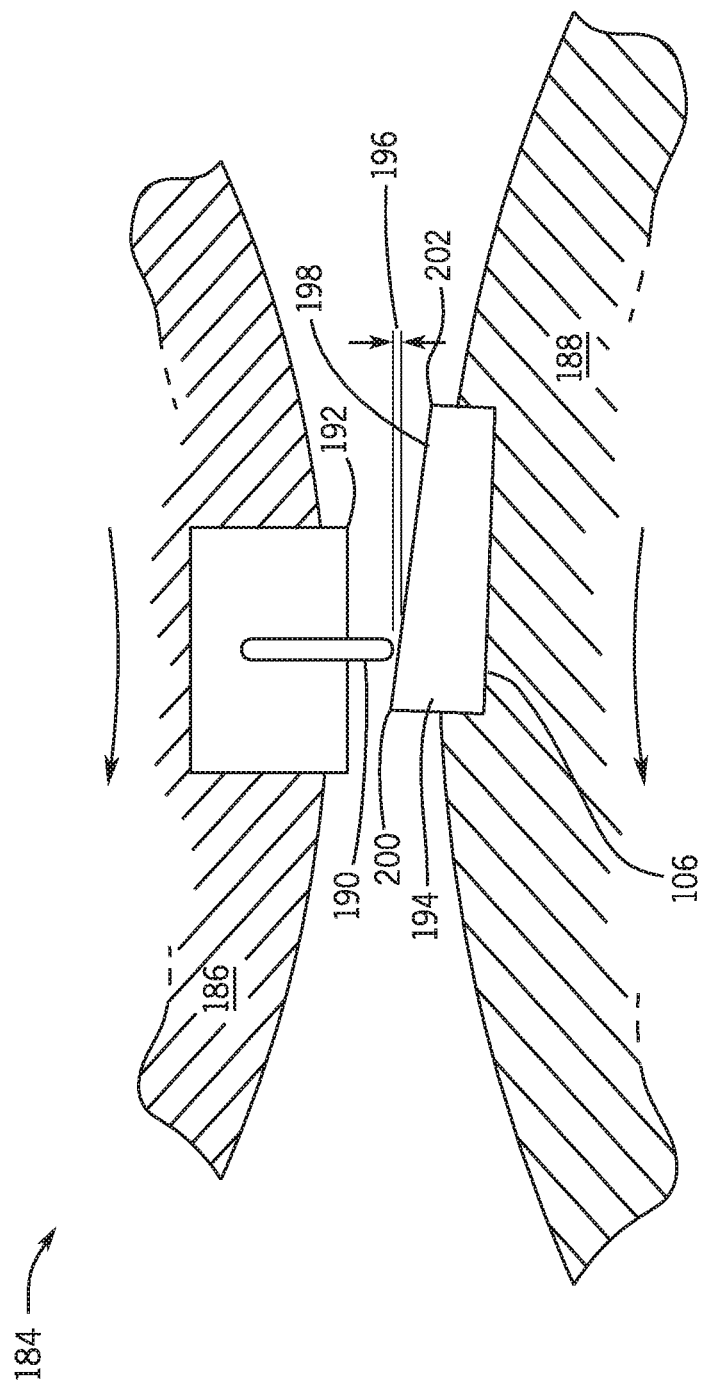
FIG. 24 is a cross-sectional view of a portion of a cutting unit usable to manufacture an elastic composite structure in accordance with the technique of FIG. 23, according to one embodiment of the invention.
Figure 26:
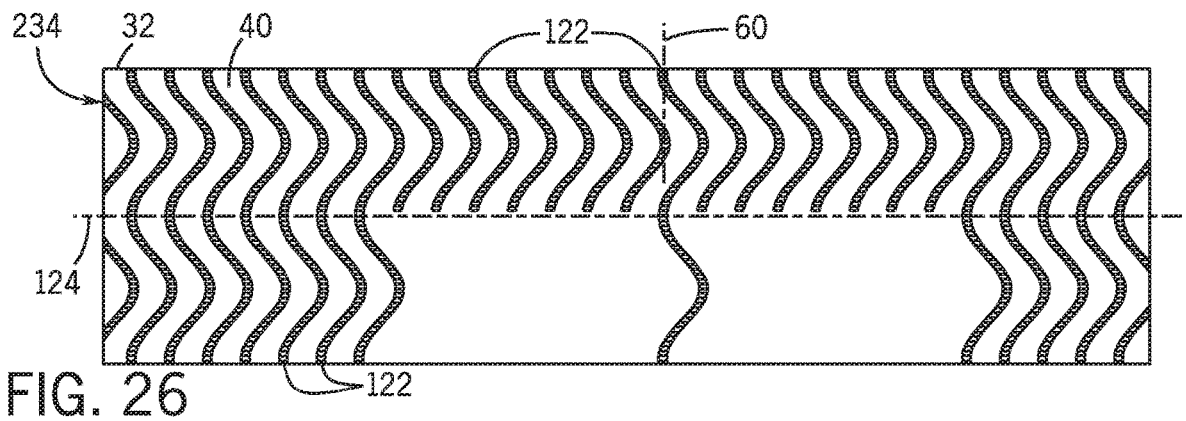
FIG. 26 is a flattened representation of an exemplary anvil pattern on a first rotary anvil that may be used to manufacture an elastic composite structure in accordance with the technique of FIG. 25, according to one embodiment of the invention.
Figure 27:
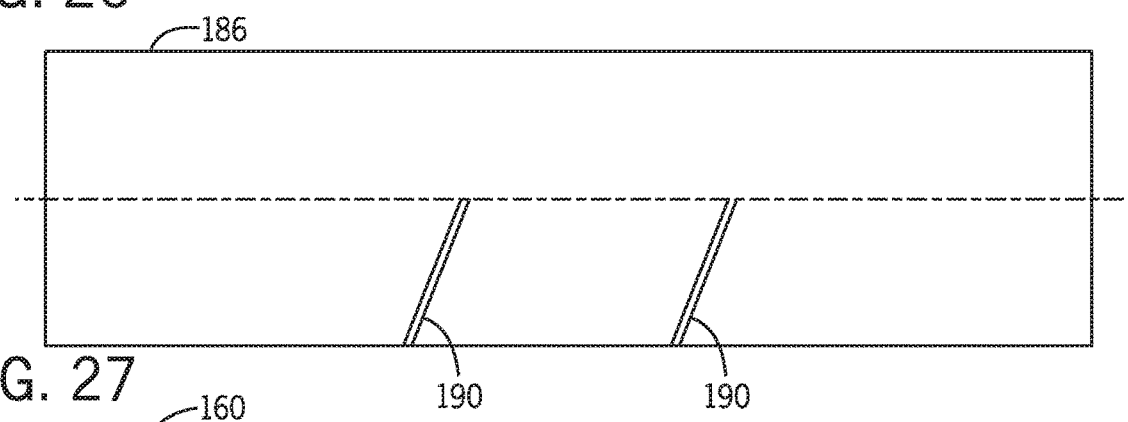
FIG. 27 is a flattened representation of the circumferential face of a cutting unit usable to manufacture an elastic composite structure in accordance with the technique of FIG. 25, according to one embodiment of the invention.
Figure 28:
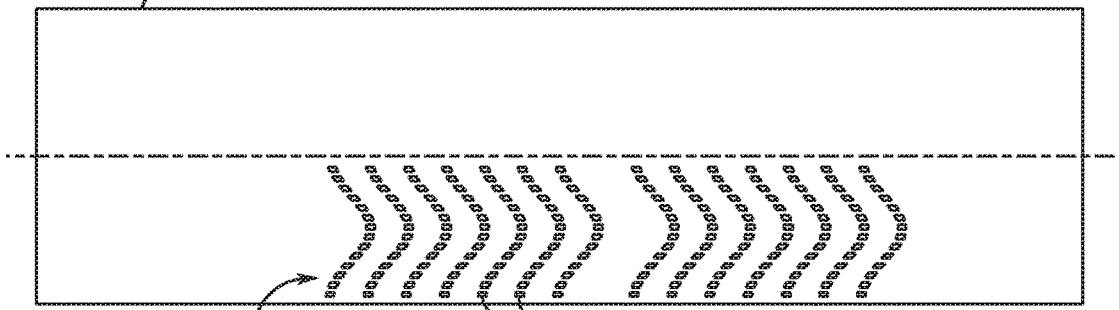
FIG. 28 is a flattened representation of an exemplary anvil pattern on a second rotary anvil that may be used to manufacture an elastic composite structure in accordance with the technique of FIG. 25, according to one embodiment of the invention.
Figure 29:
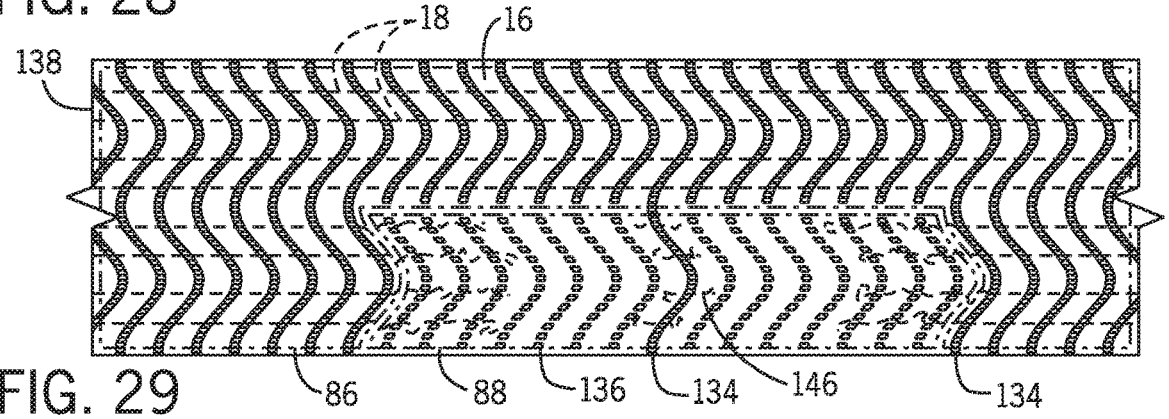
FIG. 29 is a top view of a portion of an elastic composite structure manufactured using the rotary anvils of FIGS. 26 and 28 and the cutting unit of FIG. 27, according to an embodiment of the invention.

FIGS. 26, 27, and 28 are exemplary flattened representations of the respective faces of first anvil 32, knife unit 186 (of cutting unit 184—FIG. 1), and second anvil 160 according to another alternative embodiment where the first anvil 32, knife unit 186, and second anvil 160 are positioned in the series arrangement shown in FIG. 1 and operated according to a method that produces the elastic composite structure 138 shown in FIG. 29. First anvil 32 includes a first pattern of projections 234 that includes anchoring weld lines 122 that create the anchoring bond lines 134 in FIG. 29. In the illustrated embodiment, knife unit 186 includes two knives 190 that are oriented at an angle relative to the rotational axis of the knife unit 186. In such case, the corresponding anvil inserts 194 (FIG. 24) may be arranged at a similar angle relative to the rotational axis of the rotary anvil 188 (FIG. 24). Knives 190 of knife unit 186 cut the elastic threads 18 and form the deactivated zone 88 of elastic composite structure 138. The second anvil 160 (FIG. 28) includes a second pattern of projections 236 with a series of laminating weld lines 130 that forms a series of laminating bond lines 136 (FIG. 29) within the deactivated zone 88.

Figure 30:
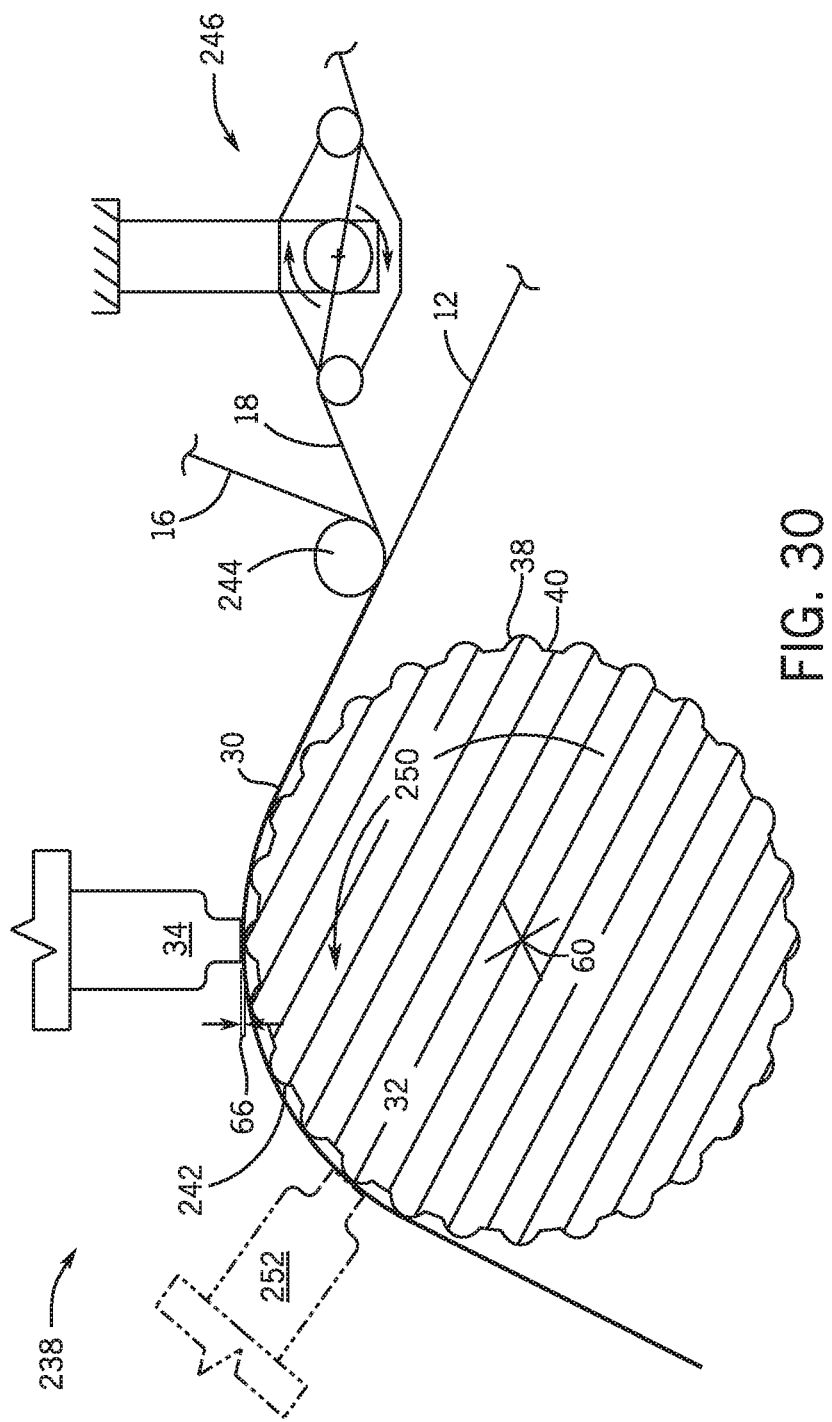
FIG. 30 is a schematic cross-sectional view of a bonding apparatus usable with the manufacturing line of FIG. 1, according to embodiments of the invention.
Figure 31:
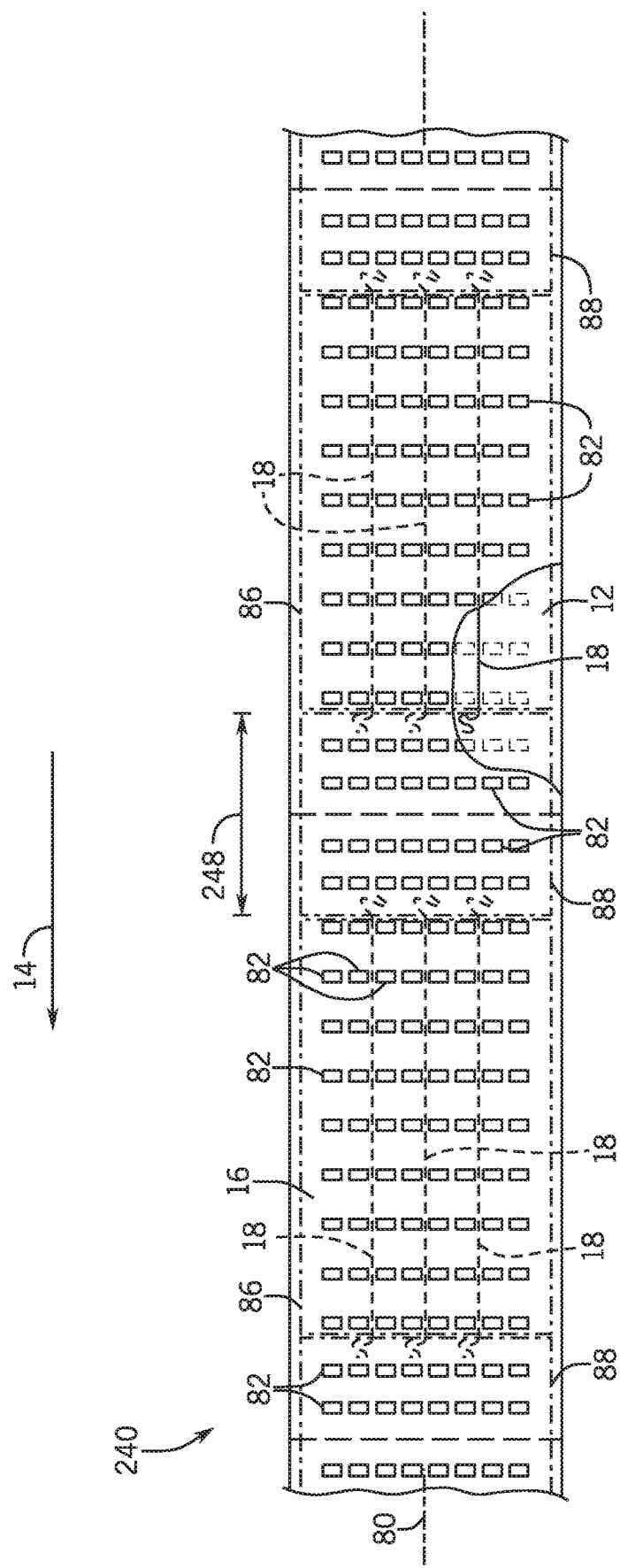
FIG. 31 is a top view of a continuous elastic composite structure manufactured using the bonding apparatus of FIG. 30, according to one embodiment of the invention.

FIG. 30 depicts a bonding apparatus 238 that can be used in manufacturing line 10 in place of bonding apparatus 22 to create an elastic composite structure 240 such as that shown in FIG. 31. In one embodiment, bonding apparatus 238 includes horn 34, as described above, and an anvil 32 that includes at least one break bar 242 that spans the length of the pattern of anchoring welds 38 on the anvil 32, similar to break bar 46 (FIG. 2), or only a portion of the overall length, similar to break bar 128 (FIG. 10). The first and second web layers 12, 16 and one or more tensioned elastic threads 18 are directed onto the face 40 of anvil 32 and into the gap 66 between anvil 32 and horn 34 either by a common guiding roller 244 or multiple rollers similar to those shown in FIG. 3. As one or more elastic threads 18 pass between a break bar 242 and horn 34, the thread(s) 18 are cut. Immediately following the cut, a tensioning device 246 increases the tension of the cut thread(s) 18 so that they are pulled backward (upstream) across the face 40 of the anvil 32 toward the common guiding roller 244. Frictional forces between the cut elastic thread(s) 18 and the first and second web layers 12, 16 prevent the cut elastic thread(s) 18 from retracting to a position upstream of the guiding roller(s) 244. As the cut thread(s) 18 are retracted to a distance equal to the desired length 248 of the deactivated zone 88 via tensioning device 246, anvil 32 continues to rotate in direction 250 and anchoring bonds 82 are formed that fuse the first and second web layers 12, 16 as the horn 34 engages anchoring welds 38 on the face 40 of anvil 32. The deactivated zone 88 shown in FIG. 31 is formed during the time period in which tensioning device 246 maintains the cut thread(s) 18 in a retracted position.

After a predetermined period of time has elapsed during which the cut thread(s) 18 retract to the trailing edge of the deactivated zone 88, the tensioning device 246 adjusts the tension in the cut elastic thread(s) 18 to the original tensioned state, causing the cut elastic thread(s) 18 to resume downstream travel toward the horn 34. After the severed end(s) of the cut elastic thread(s) 18 reach the horn 34, they effectively rethread and are anchored in place relative to the first and second web layers 12, 16 by subsequently formed anchoring bonds.

In an alternative embodiment, horn 34 is replaced by a cutting knife (for example cutting unit 184 of FIG. 24) and a horn 252 is positioned downstream of the cutting knife. One or more elastic threads 18 is severed using the cutting knife and subsequently slipped backward toward guiding roller(s) 244 by tensioning device 246 in a similar manner as described above. Once the cut elastic thread(s) 18 slips a distance equal to the length of the desired deactivated zone, tensioning device 246 adjusts the tension in the cut elastic thread(s) 18 so that the cut elastic thread(s) 18 resume travel between the first and second web layers 12, 16 across the anvil face 40. Interaction between the horn 252 and anchoring welds 38 creates anchoring bonds 82 on the resulting elastic composite structure 240.

In yet another alternative embodiment, tensioning device 246 is omitted and guiding roller 244 is replaced with an eccentric roller tensioner (not shown) that rotates to increase and decrease tension in the combined web/thread assembly 30 according to a timing pattern that is synchronized with when the elastic thread(s) 18 break. More specifically, eccentric roller tensioner is controlled to a decrease tension in the combined web/thread assembly 30 at or shortly after the time that the elastic thread(s) 18 are cut. Decreasing the tension in the combined web/thread assembly 30 reduces friction between the cut elastic thread(s) 18 and the first and second web layers 12, 16, which allows the cut elastic thread(s) 18 to snap back toward the eccentric roller tensioner. Once the cut elastic thread(s) 18 slips a distance equal to the length of the desired deactivated zone, the eccentric roller tensioner is controlled to rotate to increase tension in the combined web/thread assembly 30, thereby increasing friction between the cut elastic thread(s) 18 and the first and second web layers 12, 16. The increased friction causes the cut elastic thread(s) 18 to resume travel along with the first and second web layers 12, 16 across the anvil face 40. A deactivated zone 88 (FIG. 31) that is free of elastic thread(s) 18 but includes bonds spaced at a similar spacing as anchoring bonds 82 is formed on the resulting elastic composite structure 240 in time interval during between when the cut elastic thread(s) 18 are cut and subsequently rethread.

The apparatus and methods described herein can be used to make elastic composite structures for waist regions, below-waist regions, and/or leg cuff regions of a single-piece or three-piece diaper, as non-limiting examples, without the use of glue. By eliminating the use of glue, the resulting elastic composite is softer to the touch and has a more uniform ruffling pattern in the cross-machine direction. The apparatus and methods described herein also provide various means for forming distinct elasticized (i.e., anchored) zones and non-elasticized (i.e., deactivated) zones in the resulting elastic composite without creating cuts or slits in the web layers. Accordingly, embodiments of the invention disclosed herein enable a manufacturing process that creates an end product that is structurally more robust and visually and tactilely more pleasing to the end customer than prior art approaches.

Therefore, according to one embodiment of the invention, a bonding apparatus is disclosed for manufacturing an elastic composite structure having at least one elastic thread secured between a pair of facing web layers. The bonding apparatus includes a rotary anvil having a face with weld pattern comprising at least one anchoring region and at least one deactivating region. The at least one anchoring region includes a plurality of anchoring welds constructed to form anchoring bonds that fuse the pair of facing web layers together and anchor the at least one elastic thread in position relative to the pair of facing web layers. The at least one deactivating region includes a break bar constructed to sever the at least one elastic thread.

According to another embodiment of the invention, a method of manufacturing an elastic composite structure includes positioning a tensioned elastic thread between a first web layer and a second web layer and fusing the first web layer to the second web layer to form an anchored zone comprising a plurality of discrete anchoring bonds that fuse the first web layer to the second web layer and anchor the tensioned elastic thread therebetween. The method also includes cutting the tensioned elastic thread to form a deactivated zone of the elastic composite structure that is free of the tensioned elastic thread, the deactivated zone positioned between adjacent portions of the anchored zone. The method further includes fusing the first web layer to the second web layer within the deactivated zone.

According to yet another embodiment of the invention, an elastic composite structure includes a tensioned elastic thread, a first web layer positioned on a first side of the tensioned elastic thread, a second web layer positioned on a second side of the tensioned elastic thread, and a pattern of bonds that fuses the first web layer to the second web layer. The pattern of bonds includes a deactivated zone that includes at least one bond of the pattern of bond, a cut end of a first portion of the tensioned elastic thread, and a cut end of a second portion of the tensioned elastic thread. The deactivated zone is free of the tensioned elastic thread. The pattern of bonds also includes an anchored zone bounding opposing ends of the deactivated zone. The anchored zone includes a first plurality of bonds of the pattern of bonds that anchor the first portion of the tensioned elastic thread to the first and second web layers and a second plurality of bonds of the pattern of bonds that anchor the second portion of the tensioned elastic thread to the first and second web layers.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A bonding apparatus comprising:
   a rotary anvil comprising:
   a plurality of anchoring projections positioned in an anchoring region of the rotary anvil and constructed such that adjacent anchoring projections fuse a pair of facing web layers together with pairs of adjacent anchoring bonds that anchor an elastic thread passing between the adjacent anchoring bonds in position relative to the pair of facing web layers, the plurality of anchoring projections arranged in a plurality of anchoring weld lines spaced apart along a circumferential axis of a face of the rotary anvil; and
   a break bar that extends outward from the face of the rotary anvil in a deactivating region of the rotary anvil and is constructed to sever the elastic thread, the break bar having a length in a circumferential direction that spans at least two of the plurality of anchoring weld lines.

2. The bonding apparatus of claim 1 further comprising a horn having a working surface spaced apart from a working surface of the break bar and from land surfaces of the plurality of anchoring projections.

3. The bonding apparatus of claim 2 further comprising a mechanical camshaft assembly coupled to the horn and configured to oscillate the horn between a lowered position wherein the horn communicates with the rotary anvil to form anchoring bonds and a raised position wherein the horn is spaced away from the rotary anvil at a distance that prevents formation of anchoring bonds.

4. The bonding apparatus of claim 1 further comprising a tensioning device configured to selectively cause an elastic thread severed by the break bar to snap back in a downstream direction relative to upstream travel of the pair of facing web layers and resume downstream travel between the pair of facing web layers after a predetermined period of time.

5. The bonding apparatus of claim 1 wherein the deactivating region further comprises a plurality of laminating projections constructed to form laminating bonds that fuse the pair of facing web layers together without anchoring one or more elastic threads in position relative to the pair of facing web layers.

6. The bonding apparatus of claim 5 wherein the plurality of anchoring projections and the plurality of laminating projections are arranged in weld lines that define an overall pattern on a face of the rotary anvil.

7. The bonding apparatus of claim 5 wherein adjacent laminating projections of the plurality of laminating projections are spaced apart at a greater distance than adjacent anchoring projections of the plurality of anchoring projections.

8. The bonding apparatus of claim 1 wherein the break bar is further constructed to form a bond between the pair of facing web layers.

9. The bonding apparatus of claim 1 wherein the break bar includes a least one groove comprises a continuous weld projection that forms an unbroken bond pattern.

* * * * *

UNITED STATES PATENT AND TRADEMARK OFFICE
CERTIFICATE OF CORRECTION

PATENT NO. : 11,701,268 B2
APPLICATION NO. : 16/260259
DATED : July 18, 2023
INVENTOR(S) : Andrews et al.

Page 1 of 1

It is certified that error appears in the above-identified patent and that said Letters Patent is hereby corrected as shown below:

In the Claims

In Column 19, Claim 9, Line 17, before "comprises", delete "includes a least one groove".

Signed and Sealed this
Second Day of September, 2025

Coke Morgan Stewart
*Acting Director of the United States Patent and Trademark Office*